United States Patent
Stevens et al.

(10) Patent No.: US 9,957,288 B2
(45) Date of Patent: May 1, 2018

(54) PYRABACTIN ANALOGUES TO MODULATE PLANT DEVELOPMENT

(71) Applicant: Universiteit Gent, Ghent (BE)

(72) Inventors: Christian Stevens, Merelbeke (BE); Danny Geelen, Ghent (BE); Thomas Heugebaert, Kortrijk (BE); Inge Verstraeten, Sint-Niklaas (BE)

(73) Assignee: Universiteit Gent, Ghent (BE)

( * ) Notice: Subject to any disclaimer, the term of this patent is extended or adjusted under 35 U.S.C. 154(b) by 16 days.

(21) Appl. No.: 15/112,539

(22) PCT Filed: Jan. 27, 2015

(86) PCT No.: PCT/EP2015/051535
§ 371 (c)(1),
(2) Date: Jul. 19, 2016

(87) PCT Pub. No.: WO2015/113944
PCT Pub. Date: Aug. 6, 2015

(65) Prior Publication Data
US 2016/0333035 A1 Nov. 17, 2016

(30) Foreign Application Priority Data

Jan. 28, 2014 (EP) .................... 14152795

(51) Int. Cl.
*A01N 57/06* (2006.01)
*A01N 25/02* (2006.01)
*A01N 57/30* (2006.01)
*C07F 9/58* (2006.01)
*A01N 57/32* (2006.01)

(52) U.S. Cl.
CPC .............. *C07F 9/581* (2013.01); *A01N 57/06* (2013.01); *A01N 57/30* (2013.01); *A01N 57/32* (2013.01); *C07F 9/588* (2013.01)

(58) Field of Classification Search
None
See application file for complete search history.

(56) References Cited

U.S. PATENT DOCUMENTS 5,266,552 A * 11/1993 Broadhurst ............ A01N 57/30
504/199

OTHER PUBLICATIONS

Puli et al., "Pyrabactin, an ABA agonist, induced stomatal closure and change in signalling components of guard cells in abaxial epidermis of Pisum sativum", XP-055177285, Journal of Experimental Botany, vol. 63, No. 3, pp. 1349-1356, 2012.
International Search Report and Written Opinion dated Apr. 7, 2015 pertaining to PCT/EP2015/051535 filed Jan. 27, 2015.
Ashokan, K.V., Docking Studies on a Abscisic Acid Receptor Pyrabactin Receptor 1 (pyr1) and Pyrabactin Like Receptor 1(pyl1), International Journal of Environmental Sciences, vol. 1, Issue 3, Research Article ISSN 0976-4402, 2010, pp. 314-322.
Peterson, Francis C., et al., Structural Basis for Selective Activation of ABA Receptors, HHS Public Access Author Manuscript, Nat. Struct. Nol. Biol., Mar. 1, 2011, pp. 1-14.
Park, Sang-Youl, et al., Abscisic Acide Inhibits Type 2C Protein Phosphatases via thePYR/PYL Family of START Proteins, www.sciencemag.org, vol. 324, May 22, 2009, pp. 1068-1071.
Hao, Qi, et al., Functional Mechanism of the Abscisic Acid Agonist Pyrabactin, Journal of Biological Chemistry, vol. 285, No. 37, Sep. 10, 2010, pp. 28946-28952, Supplementary Figures 1-6.

* cited by examiner

*Primary Examiner* — Alton N Pryor
(74) *Attorney, Agent, or Firm* — Dinsmore & Shohl LLP

(57) ABSTRACT

The present invention relates to compounds which can be used to control plant development. Indeed, the present invention discloses a new class of pyrabactin analogues which have a physiological effect on—for example—seed germination, and/or stomatal closure, and/or have developmental effects on root and shoot development and organogenesis. Hence, the latter compounds can be used to control plant development such as—for example—increasing the tolerance of plants to drought stress or to control physiological phenomena such as pre-harvest sprouting, tolerance to pathogens etc.

8 Claims, 10 Drawing Sheets

PYRABACTIN ANALOGUES TO MODULATE PLANT DEVELOPMENT

TECHNICAL FIELD OF INVENTION

The present invention relates to compounds which can be used to control plant development. Indeed, the present invention discloses a new class of pyrabactin analogues which have a physiological effect on—for example—seed germination, and/or stomatal closure, and/or have developmental effects on root and shoot development and organogenesis. Hence, the latter compounds can be used to control plant development such as—for example—increasing the tolerance of plants to drought stress or to control physiological phenomena such as pre-harvest sprouting, tolerance to pathogens etc.

BACKGROUND ART

With the ongoing climate changes and raise of population, the demands of crop yield are continuously increasing (International Panel on Climate Change, 2007; Tilman et al, 2011). In addition to minimizing $CO_2$-emissions from agriculture, developing crops that cope better with suboptimal growth conditions, like drought, salinity and increasing temperatures is necessary. Manipulations or control of the development of—and signaling in plants are ways to improve the tolerance responses in plants and to ensure their flexibility in a changing environment without negative effects on yield. Although treatments of plants with exogenous plant hormones such as abscisic acid (ABA) have been shown to improve stress tolerance, the use of ABA by topical spraying, to protect plants against the effects of drought conditions is limited because of pleiotropic side-effects, such as an inhibited primary root growth (Sreenivasulu et al, 2012). Moreover, ABA is light-sensitive and degrades rapidly when in contact with plants (Hao et al, 2010). These drawbacks stimulated the screening for new molecules that switch on the ABA-signaling pathway more specifically, without the side-effects and with better stability to make applications in agriculture feasible (Joshi-Saha et al, 2011; Melcher et al, 2009).

In 2009, a chemical genetics screen resulted in the identification of an ABA-agonist: pyrabactin, which is structurally not related to ABA (Park et al, 2009). Microarray analysis of ABA-responses in seeds and seedlings suggested that pyrabactin is a selective agonist of ABA (Kitahata & Asami, 2011; Park et al, 2009). The further screening of pyrabactin-resistant mutants made it possible to identify a family of ABA-receptor proteins: the PYR1/PYL/RCAR START proteins (Kitahata & Asami, 2011; Park et al, 2009). Although there are no apparent chemical or structural similarities between the sulphonamide pyrabactin and ABA, they both act through the PYR/PYL receptor family (Hao et al, 2010). However, pyrabactin does not provoke all the responses described for ABA (Park et al, 2009; Peterson et al, 2010). Furthermore, also the interaction with the receptors differs between the two molecules. Pyrabactin acts as an antagonist of PYL2, which means that pyrabactin-binding in the receptor does not stimulate the attraction of PP2Cs and thereby does not remove the inhibitory factors for downstream signaling. This is in contrary to ABA, which is an agonist of this receptor (Melcher et al, 2010a; Mosquna et al, 2011). This observation suggests that pyrabactin differentially modulates ABA-receptors activity and may even target only a subgroup of receptors. However, since its discovery, pyrabactin has not been applied to improve crop production in for example drought conditions. Sulphonamides have indeed been described to have negative effects on plant growth and are even used as herbicides (Audus & Quastel, 1948; Crowdy & Jones, 1956). Moreover, the effects of pyrabactin in vegetative tissue are limited and the ABA-agonist activity is specific to seeds.

Alternative compounds to pyrabactin with improved chemical properties are thus highly needed.

DESCRIPTION OF INVENTION

Figure 1:
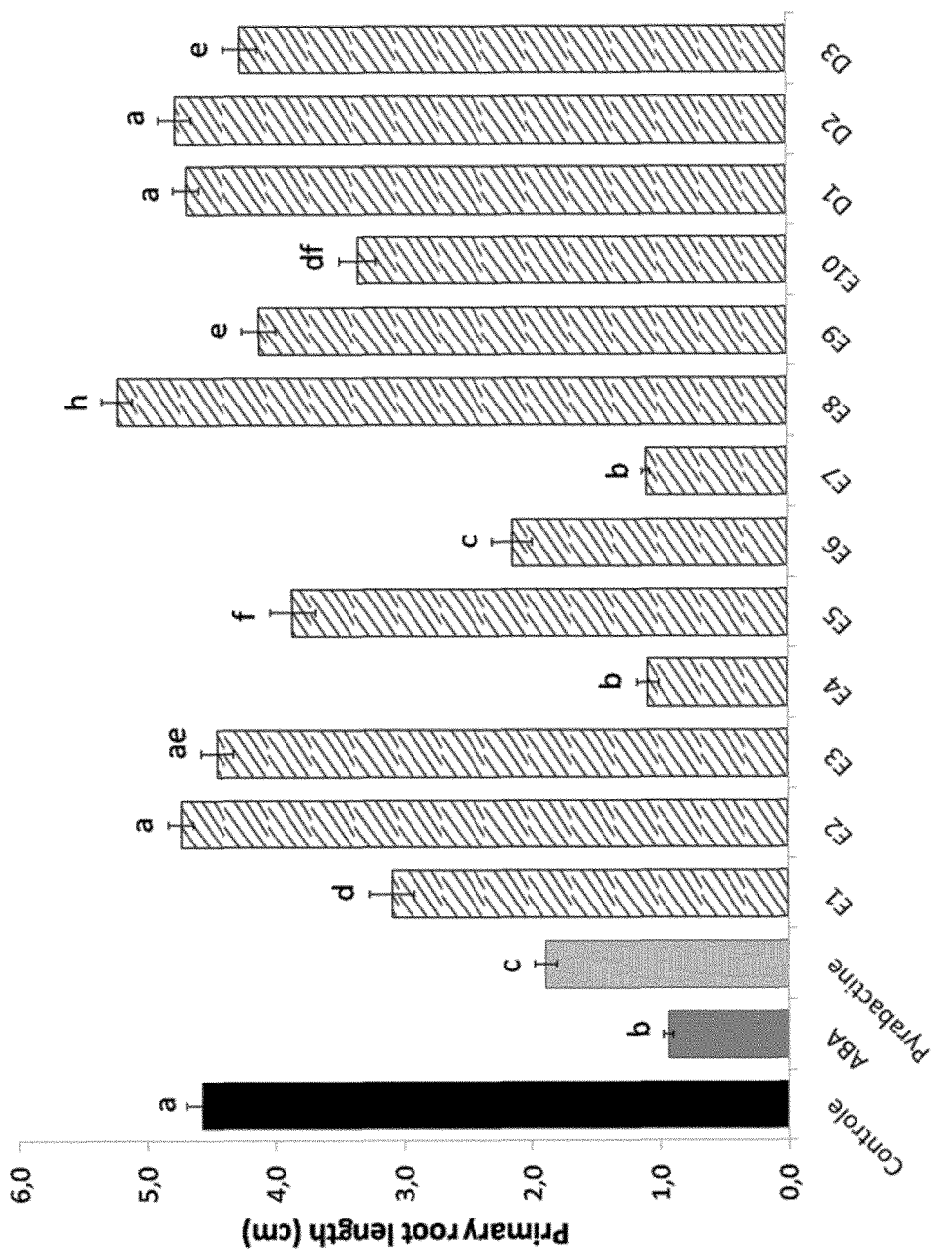
FIG. 1: Effect on primary root elongation of ABA, pyrabactin and the different analogues at 10 μM concentration.

The present invention relates in essence to the replacement of the sulphonamide group within pyrabactin by a phosphonamide group. Since phosphorous is one of the essential elements for optimal plant growth, the phosphonamide functional group is a favorable alternative for sulphonamides, as plants are better equipped for their uptake. The biocompatibility with plant enzymes is also better adapted for phosphate-based products than for sulphates. Despite the substitution of sulphur with phosphor receptor, binding can be maintained due to their similar molecular weight and geometry. Moreover, the formation of hydrogen-bonds in the binding cavity of the receptors might occur via the two oxygen substitutions present both on the sulphonamide and the phosphonamide. Both molecules have a comparable solvability, polarity and are similarly affected by different pH. All these characteristics are favorable for the biological activity of these molecules.

The present invention thus relates to phosphonamide-containing compounds which can be used to control a pathway involved in plant development. The terms 'a pathway involved in plant development' relate to a series of transitory states of gene and protein expression, biochemicals and physiological conditions that lead to the formation of new organs and structures of a plant.

The term 'plant' includes whole plants, shoot vegetative organs and/or structures (e.g. leaves, stems and tubers), roots, flowers and floral organs, ovules, seeds, fruit, seedlings, plant tissue, cells and progeny of same. The class of plants is generally as broad as the class of higher and lower plants including angiosperms (monocotyledonous and dicotyledonous plants), gymnosperms, ferns and multicellular algae.

The present invention discloses a new class of pyrabactin analogues which have a physiological effect on—for example—seed germination, and/or stomatal closure, and/or have developmental effects on root and shoot development and organogenesis. Hence, the latter compounds can be used to control plant development such as—for example—increasing the tolerance of plants to drought stress or to control physiological phenomena such as pre-harvest sprouting, tolerance to pathogens etc.

The term 'shoot development' relates to the expansion of the shoot biomass by cell division and cell expansion at the apical meristem, the axillary meristem and de novo formed adventitious shoots.

The present invention thus relates to a compound—or its salt—of the formula:

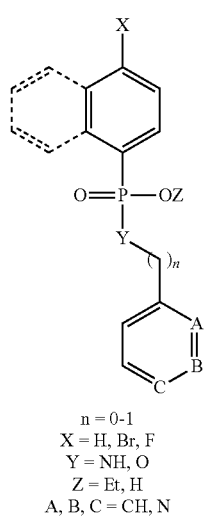

n = 0-1
X = H, Br, F
Y = NH, O
Z = Et, H
A, B, C = CH, N

The latter formula thus represents a generic formula of the claimed compounds.

The present invention more specifically relates to the compounds denominated as E2, E3, E5 or E8 and having the following formula:

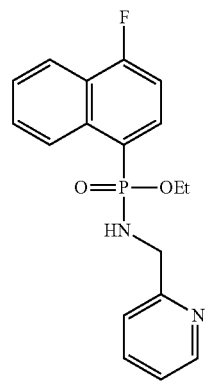

E2

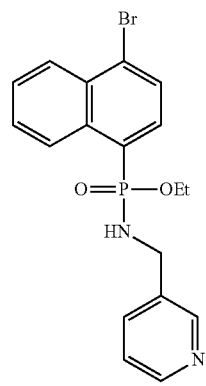

E3

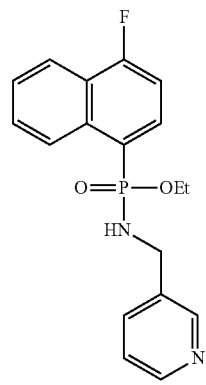

E5

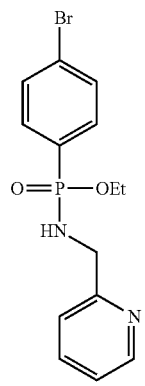

E8

The present invention further relates to a method to synthesize a compound as described above comprising:
phosphonylating a suitable halogenated benzene or naphthalene precursor by means of lithium halogen exchange and subsequent diethylchlorophosphate quench in order to obtain diethyl phenyl- or naphtylphosphonate intermediates, monodealkylating said diethyl phenyl- or naphtylphosphonate intermediates by means of basic hydrolysis conditions in order to obtain phosphonic acid intermediates, activating said phosphonic acid intermediates to their corresponding chlorophosphonates by means of thionylchloride, and, performing a nucleophilic displacement of said chloride under basic conditions by means of a suitable benzyl-(n=1) or phenyl-(n=0) amine (Y=NH) or alcohol (Y=O). (Y=O), interchanging the remaining phosphonate alkoxy group for a hydroxyl group by means of basic, lithium hydroxide mediated hydrolysis.

In other words, the present invention relates to a method to synthesize the compound as described above comprising (see also further in the Examples section: 'General scheme for the synthesis of compounds E and D, and their respective intermediates 2, 3 and 3'):

Step 1: The phosphonylation of a suitable halogenated benzene or naphthalene (precursor 1, see General scheme) by means of lithium halogen exchange and subsequent diethylchlorophosphate quench. Substrate dependent temperature, time and addition order regimes which avoid both dual lithiation, dual phosphonate alkylation and alkyl lithium addition to the resulting phosphonate are described further in the examples section.

Step 2: The monodealkylation of diethyl phenyl- or naphtylphosphonates (intermediates 2, as obtained from step 1) by means of basic hydrolysis conditions, resulting in phosphonic acids (intermediate 3). Complete and clean conversions were obtained, in line with the reports of Mucha and Xie (Mucha, 2006; Xie, 2009). Acid-base extraction provides a convenient method of isolation.

Step 3: The activation of phosphonic acids 3 as obtained from step 2 to their corresponding chlorophosphonates 3' by means of thionylchloride (step 3a). Nucleophilic displacement of said chloride under basic conditions (step 3b) by means of a suitable benzyl-(n=1) or phenyl-(n=0) amine (Y=NH) or alcohol (Y=O) delivers the claimed compounds such as the compounds denominated as E1, E2, E3, E4, E5, E6, E7, E8, E9 and E10, and, D 1, D2 and D3 (see further in examples section) in moderate to good yield. The activation step and nucleophilic displacement step are combined as intermediate 3' does not have to be isolated.

Step 4: The lithium hydroxide mediated interchange of the remaining phosphonate alkoxy group for a hydroxyl group.

The present invention further relates to the usage of compound 'E2', 'E3' and 'E8' to specifically induce stomatal closure without affecting root or shoot growth.

The term 'stomatal closure' refers to the turgor pressure loss in guard cells that lead to a reduction in stomatal conductance, determining the rate of passage of carbon dioxide, oxygen and water vapor through the stomata of a leaf.

The term 'root growth' refers to the expansion of the root biomass mediated by cell division and cell expansion in the primary meristem and in de novo initiated lateral and adventitious root meristems.

The term 'shoot growth' refers to the expansion of the shoot biomass by cell division and cell expansion at the apical meristem, the axillary meristem and the de novo formed adventitious shoots.

Stomatal closure is typically induced by conditions of drought or can be mimicked under normal water conditions by spraying leaves with a solution of abscisic acid at a concentration between 1-10.000 ppm, this with the aim to increase water conservation (Daszkowska-Golec and Szarejko, 2013). The E2 compound can be applied using similar spraying technology to achieve the same, with the main difference that E2 does not exert root or shoot growth inhibition, but on the contrary supports regular root growth, which promotes tolerance to future drought conditions conditions and the access to deeper water resources.

The present further relates to the usage of compound 'E5' to specifically inhibit seed germination.

The term 'seed germination' relates to the transition of a dormant state to an actively growing state during which the embryo develops into a seedling. In some crops loss of seed dormancy due to domestication and breeding, causes premature germination leading to poor grain quality and economic losses.

Soaking, imbibing or other types of seed treatments such as coating with solutions containing abscisic acid suppress seed germination (Zhang et al., 2010). In a similar approach the compound E5 can be applied in spraying, imbibition or coating solutions.

The present invention thus also relates to an agricultural chemical formulation formulated for contacting to plants, the formulation comprising a compound as described above.

The formulations are thus suitable for treating plants or plant propagation material such as seeds. Suitable additives include buffering agents, coating agents, polysaccharides and abrading agents. Exemplary carriers include water, aqueous solutions, slurries, solids and dry powders. Optionally, the formulations can also include at least one surfactant, herbicide, fungicide, pesticide or fertilizer. Hence, the present invention relates to a formulation as described above further comprising at least one of a herbicide, fungicide, pesticide, fertilizer or surfactant.

The present invention further relates to a method of modulating plant development, the method comprising contacting a plant with a sufficient amount of the formulation as described above to modulate the development of said plant compared to not contacting the plant with said formulation.

The term 'plant development' is defined by the growth of a plant through cell division and cell expansion. These processes occur in a coordinated and organized manner within meristems at certain locations in the plant body. Meristems generate new organs be it in the root or the shoot part of the plant. The control of cell division and expansion in meristems determines the architecture of a plant. Plant development also encompasses the transition of one ontogenic state to another such as for example the vegetative phase to the regenerative phase.

The term 'modulate' means to change, to regulate, to influence and/or to adjust plant development.

The present invention further relates to a method as described above wherein said modulation is increasing the tolerance to drought stress.

The term 'stress' relates to a molecular, biochemical and physiological state evoked by unfavorable environmental conditions. A stress response refers to the molecular, biochemical and physiological changes that are induced by the changed environmental condition.

The term 'drought stress' relates to a physiological state of a plant that is exposed to conditions of reduced water availability. Drought stress is often accompanied by physical and biochemical changes or damage of the plant of plant structures. These include wilting, reduced photosynthesis, and temporarily increased root growth, arrest of shoot development.

The term 'tolerance to drought stress' relates to a genetic, biochemical and physiological adaptations a plant undergoes to withstand periods of drought.

The present invention will now be illustrated by the following, non-limiting examples.

EXAMPLES

Material and Methods

1. Synthesis of the Phosphonamide Analogues of the Present Invention

The chemical synthesis and structures of the 13 phosphonamide analogues (denominates as E1-E10 and D1-D3, see 'E' and 'D' in figures) as well as their synthetic intermediates 2, 3 and 3' are given in the 'General scheme for the synthesis of compounds E and D, and their respective intermediates 2, 3 and 3' as given hereunder:

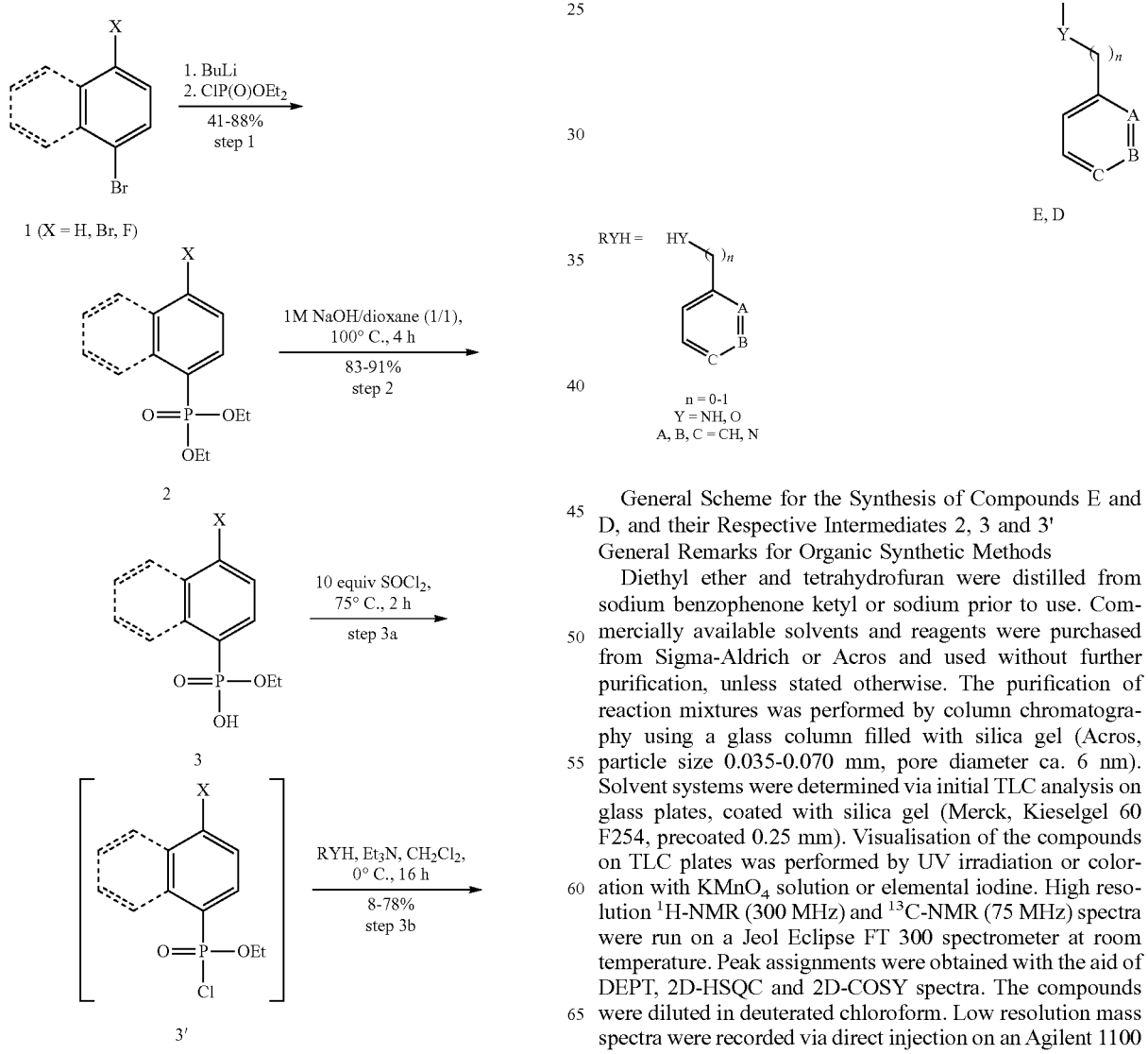

General Scheme for the Synthesis of Compounds E and D, and their Respective Intermediates 2, 3 and 3'

General Remarks for Organic Synthetic Methods

Diethyl ether and tetrahydrofuran were distilled from sodium benzophenone ketyl or sodium prior to use. Commercially available solvents and reagents were purchased from Sigma-Aldrich or Acros and used without further purification, unless stated otherwise. The purification of reaction mixtures was performed by column chromatography using a glass column filled with silica gel (Acros, particle size 0.035-0.070 mm, pore diameter ca. 6 nm). Solvent systems were determined via initial TLC analysis on glass plates, coated with silica gel (Merck, Kieselgel 60 F254, precoated 0.25 mm). Visualisation of the compounds on TLC plates was performed by UV irradiation or coloration with $KMnO_4$ solution or elemental iodine. High resolution $^1$H-NMR (300 MHz) and $^{13}$C-NMR (75 MHz) spectra were run on a Jeol Eclipse FT 300 spectrometer at room temperature. Peak assignments were obtained with the aid of DEPT, 2D-HSQC and 2D-COSY spectra. The compounds were diluted in deuterated chloroform. Low resolution mass spectra were recorded via direct injection on an Agilent 1100 Series LC/MSD type SL mass spectrometer with electron spray ionisation geometry (ESI 70V) and using a mass selective detector (quadrupole). IR-spectra were obtained from a Perkin-Elmer BX FT-IR spectrometer. All compounds were analysed in neat form with an ATR (Attenuated Total Reflectance) accessory.

Synthesis of 1,4-dibromonaphtalene (Precursor 1 Containing a naphtyl core where X=Br)

In a 100 ml flask 5.00 g (0.039 mol, 1 equiv.) naphtalene is dissolved in 75 ml dichloromethane. The flask is placed under inert atmosphere and cooled to −30° C., after which 25.00 g (0.156 mol, 4 equiv.) $Br_2$ is added dropwise. Fifteen minutes after the complete addition of bromine, the reaction is continued for 72 h at room temperature. The reaction is quenched using 1M $NaHSO_3$. The organic phase is dried by means of $MgSO_4$ and the volatiles are evaporated. The compound is crystallised using cold dichloromethane (−18° C.), by slow addition of hexanes, resulting in a yield of 70%. From the mother liquor, an additional 17% could be recuperated by column chromatography using hexanes.

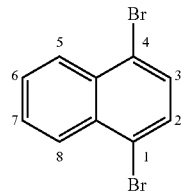 [SMILES: Brc1ccc(Br)c2ccccc12]

$^1$H-NMR (300 MHz, $CDCl_3$): δ 7.61-7.67 (4H, m, $C_2H_{arom}$, $C_3H_{arom}$, $C_6H_{arom}$, $C_7H_{arom}$); 8.22-8.28 (2H, m, $C_5H_{arom}$, $C_8H$ arom). $^{13}$C-NMR (75 MHz, $CDCl_3$): δ 122.7 (2×$C_qBr$); 127.9 ($C_5H_{arom}$, $C_8H_{arom}$); 128.3 ($C_6H_{arom}$, $C_7H_{arom}$); 130.2 ($C_2H_{arom}$, $C_3H_{arom}$); 133.0 (2×$C_qC_qBr$). IR ($cm^{-1}$) vmax: 1584; 1492. MP: 74.3-75.3° C. (hexanes). Yield: 87%.

Synthesis of diethyl 4-fluoronapht-1-ylphosphonate: General Method for the Synthesis of Intermediate 2 where X=F In a dry 250 ml flask 3.00 g (13.3 mmol, 1 equiv.) 1-bromo-4-fluoronaphtalene is dissolved in 150 ml dry diethyl ether. The mixture is placed under inert atmosphere and cooled to −78° C. Subsequently, 10 ml (0.020 mol, 1.5 equiv.) of a 2M solution of BuLi is slowly dripped in. After continuing the reaction for 1 h, 3.44 g (0.020 mol, 1.5 equiv.) diethylchlorophosphate is added at −78° C. and the mixture is allowed to warm to room temperature. After 1 h at room temperature the reaction is quenched using 200 ml aqueous saturated ammonium chloride and extracted three times by means of dichloromethane. The combined organic fractions are dried using $MgSO_4$ and the volatiles are evaporated. Purification was performed using column chromatography and the compound was isolated in 88% yield as a yellow oil.

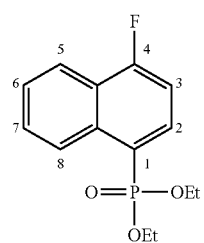

$^1$H-NMR (300 MHz, $CDCl_3$): δ 1.31 (6H, t, J=7.2 Hz, 2×$CH_3$); 4.01-4.27 (4H, m, 2×$CH_2$); 7.20 (1H, dxdxd, J=10.2 Hz, 7.7 Hz, 2.8 Hz, $C_2H_{arom}$); 7.59-7.71 (2H, m, 2×$CH_{arom}$); 8.20 (1H, dxd, J=8.0 Hz, 6.1 Hz, $CH_{arom}$); 8.25 (1H, dxd, J=8.0 Hz, 5.8 Hz, $C_3H_{arom}$); 8.52 (1H, d, J=8.0 Hz, $CH_{arom}$). $^{13}$C-NMR (75 MHz, $CDCl_3$): δ 16.4 (2×$CH_3$, d, J=6.9 Hz); 62.3 (2×$CH_2$, d, J=5.8 Hz); 108.6 ($C_2H_{arom}$, dxd, J=20.2 Hz, 17.9 Hz); 120.7 ($C_qP$, dxd, J=186.9 Hz, 4.6 Hz); 121.2 ($CH_{arom}$, d, J=6.9 Hz); 124.1 ($C_qC_qP$, t, J=15.0 Hz); 126.6 ($CH_{arom}$, t, J=3.5 Hz); 126.8 ($CH_{arom}$); 128.5 ($CH_{arom}$); 134.6 ($C_qC_qF$, dxd, J=12.7 Hz, 4.6 Hz); 135.5 ($C_3H_{arom}$, t, J=9.8 Hz); 162.1 ($C_qF$, dxd, J=259.6 Hz, 4.6 Hz). $^{19}$F-NMR (282 MHz, $CDCl_3$): δ 114.30. $^{31}$P-NMR (121 MHz, $CDCl_3$): δ 19.00. MS (ESI): m/z (%): 565 (2M+H$^+$, 35), 283 (M+H$^+$, 100). IR ($cm^{-1}$) vmax: 1164 (P—OEt); 1234 (P=O); 1628; 1600; 1573; 1509. Chromatography: hexanes/EtOAc 50/50 Rf=0.25. Yield: 88%.

Synthesis of diethyl 4-bromonapht-1-ylphosphonate: General Method for the Synthesis of Intermediate 2 where X=Br, H In a dry 250 ml flask 3.00 g (10 mmol, 1 equiv.) 1,4-dibromonaphtalene is dissolved in 150 ml dry diethyl ether. The mixture is placed under inert atmosphere and cooled to −78° C. Subsequently, 5.5 ml (0.011 mol, 1.1 equiv.) of a 2M solution of BuLi is slowly dripped in. After continuing the reaction for 30 min at −30° C., 3.44 g (0.020 mol, 1.5 equiv.), the mixture is cooled to −78° C. and added by means of a cannula to a 250 ml flask containing 17.26 g (0.1 mol, 10 equiv.) diethylchlorophosphate in diethylether at −78° C. The mixture is allowed to warm to room temperature and after 1 h it is quenched using 200 ml water. The compound is extracted three times by means of dichloromethane, the combined organic fractions are washed three times with 1M NaOH, dried using $MgSO_4$ and the volatiles are evaporated. Purification was performed using column chromatography and the compound was isolated in 74% yield as a white solid.

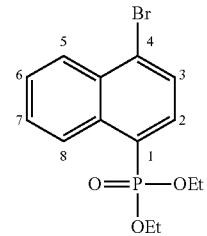 [SMILES: CCOP(=O)(OCC)c1ccc(Br)c2ccccc12]

$^1$H-NMR (300 MHz, $CDCl_3$): δ 1.31 (6H, t, J=7.2 Hz, 2×$CH_3$); 4.01-4.28 (4H, m, 2×$CH_2$); 7.66 (2H, m, 2×$CH_{arom}$); 7.87 (1H, dxd, J=7.7 Hz, 2.8 Hz, $C_3H_{arom}$) 8.08 (1H, dxd, J=16.0 Hz, 7.7 Hz, $C_2H_{arom}$); 8.32-8.37 (1H, m, $CH_{arom}$) 8.53-8.57 (1H, m, $CH_{arom}$). $^{13}$C-NMR. (75 MHz, $CDCl_3$): δ 16.4 (2×$CH_3$, d, J=6.9 Hz); 62.5 (2×$CH_2$, d, J=4.9 Hz); 124.9 ($C_qP$, d, J=184.6 Hz); 127.2 ($CH_{arom}$, d, J=3.5 Hz); 127.9 ($CH_{arom}$); 128.0 ($CH_{arom}$); 128.3 ($CH_{arom}$); 129.0 ($C_3H_{arom}$, d, J=17.3 Hz); 129.6 ($C_qC_qP$, d, J=4.6 Hz); 132.2 ($C_qC_qP$, d, J=13.9 Hz); 133.8 ($C_qC_qBr$, d, J=11.5 Hz); 134.6 ($C_2H_{arom}$, d, J=9.2 Hz). $^{31}$P-NMR (121 MHz, $CDCl_3$): δ 18.96. MS (ESI): m/z (%): 685/687/689 (2M+H$^+$, 15/30/15), 343/345 (M+H$^+$, 100/100). IR ($cm^{-1}$) vmax: 1165 (P-OEt); 1248 (P=O); 1617; 1560; 1503; 1477. MP: 56.4-56.9° C. (EtOAc). Chromatography: hexanes/EtOAc 60/40 Rf=0.23. Yield: 74%

Synthesis of diethyl napht-1-ylphosphonate: Intermediate 2 Containing a Naphtyl Core with X=H A similar procedure was used as for the synthesis of diethyl(4-bromonaftyl)phosphonate. The lithium-halogen exchange is performed at −40° C. for 90 minutes. As starting material 1 g (4.83 mmol, 1 equiv.) 1-bromonaphtalene was used. The compound was obtained in 67% yield as a yellow oil. Its purity by LC was 95%.

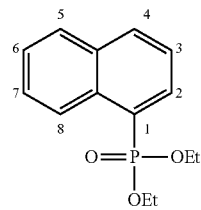

$^1$H-NMR (300 MHz, CDCl$_3$): δ 1.31 (6H, t, J=7.2 Hz, 2×CH$_3$); 4.01-4.28 (4H, m, 2×CH$_2$); 7.51-7.65 (3H, m, C$_3$H$_{arom}$, 2×CH$_{arom}$); 7.85-7.95 (1H, m, CH$_{arom}$); 8.04 (1H, d, J=8.3, CH$_{arom}$); 8.25 (1H, d×d, J=16.5 Hz, 7.2 Hz, C$_2$H$_{arom}$); 8.52 (1H, d, J=8.3 Hz, CH$_{arom}$). $^{13}$C-NMR (75 MHz, CDCl$_3$): δ 16.4 (2×CH$_3$, d, J=6.9 Hz); 62.3 (2×CH$_2$, d, 4.6 Hz); 124.6 (C$_q$P, d, J=182.3 Hz); 124.6 (C$_3$H$_{arom}$, d, J=16.2 Hz); 126.5 (CH$_{arom}$); 126.7 (CH$_{arom}$, d, J=4.6 Hz); 127.5 (CH$_{arom}$); 128.9 (CH$_{arom}$); 132.8 (C$_q$ C$_q$P, d, 11.5 Hz); 133.8 (CH$_{arom}$, d, J=3.5 Hz); 134.2 (CHC$_q$CH, d, 10.4 Hz); 134.8 (C$_2$H$_{arom}$, d, J=9.2 Hz). $^{31}$P-NMR (121 MHz, CDCl$_3$): δ 19.80. MS (ESI): m/z (%): 265 (M+H$^+$, 100); 529 (2M+H$^+$, 90). IR (cm$^{-1}$) vmax: 1163 (P-OEt); 1240 (P=O); 1477; 1508; 1571; 1591. Chromatography: hexanes/EtOAc 50/50 Rf=0.23. Yield: 67%.

Synthesis of diethyl 4-bromophenylphosphonate: Intermediate 2 Containing a Phenyl Core with X=Br A similar procedure was used as for the synthesis of diethyl(4-bromonaphtyl)phosphonate. As starting material 1.5 g (6.36 mmol, 1 equiv.) 1,4-dibromobenzene was used and the product was obtained in 41% yield as a yellow oil. It's purity by LC was 90%.

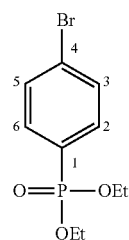 [SMILES: CCOP(=O)(OCC)c1ccc(Br)cc1]

$^1$H-NMR (300 MHz, CDCl$_3$): δ 1.32 (6H, t, J=6.9 Hz, 2×CH$_3$); 4.01-4.19 (4H, m, 2×CH$_2$); 7.59-7.72 (4H, m, 4×CH$_{arom}$). $^{13}$C-NMR (75 MHz, CDCl$_3$): δ 16.4 (2×CH$_3$, d, J=6.9 Hz); 62.4 (2×CH$_2$, d, J=5.8 Hz); 127.5 (C$_q$P, d, J=195.0 Hz); 127.6 (C$_q$Br, d, J=3.5 Hz); 131.9 (2×CHC$_q$Br, d, J=15.0 Hz); 133.4 (2×CHC$_q$P, d, J=10.4 Hz). $^{31}$P-NMR (121 MHz, CDCl$_3$): δ 18.39. MS (ESI): m/z (%): 585/587/589 (2M+H$^+$, 12/24/12), 293/295 (M+H$^+$, 100/100). IR (cm$^{-1}$) vmax: 1164 (P-OEt); 1248 (P=O); 1646; 1580; 1478; 1443. Chromatography: hexanes/EtOAc 60/40 Rf=0.23. Yield: 41%

General Procedure for the Synthesis of Intermediates 3: Arylphosphonic Acids

In a 100 ml flask 1 g phosphonate (intermediate 2) is dissolved in 25 ml dioxane. To this, 25 ml of a 1M NaOH solution is added. The reaction is heated to reflux for a period of 4 hours. The resulting mixture is washed using dichloromethane. The aqueous phase is acidified using HCl to a pH of 1. The product is extracted using three fractions of dichloromethane. The combined organic phases are washed with brine, dried using MgSO$_4$ and concentrated. Remainders of dioxane were removed by high vacuum.

Ethyl 4-fluoronapht-1-ylphosphonate: Intermediate 3 Containing a Naphtyl Core with X=F

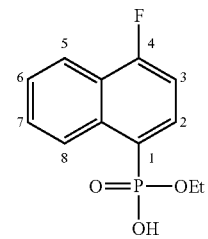 [SMILES: CCOP(=O)(O)c1ccc(F)c2ccccc12]

The compound is obtained as white crystals in a yield of 83%. $^1$H-NMR (300 MHz, CDCl$_3$): δ 1.24 (3H, t, J=6.9 Hz, CH$_3$); 4.04 (2H, m, CH$_2$); 7.08 (1H, m, C$_2$H$_{arom}$); 7.59 (2H, m, 2×CH$_{arom}$); 8.08-8.16 (2H, m, C$_3$H$_{arom}$, CH$_{arom}$); 8.50 (1H, d, J=7.7 Hz, CH$_{arom}$). $^{13}$C-NMR (75 MHz, CDCl$_3$): δ 16.3 (CH$_3$, d, J=6.9 Hz); 62.2 (CH$_2$, d, J=5.8 Hz); 108.4 (C$_2$H$_{arom}$, t, J=19.0 Hz); 121.2 (CH$_{arom}$, d, J=5.8 Hz); 121.4 (C$_q$P, d×d, J=193.8 Hz, 3.5 Hz); 124.0 (C$_q$C$_q$P, t, J=15.0 Hz); 126.8 (2×CH$_{arom}$); 128.5 (CH$_{arom}$); 134.4-134.7 (C$_3$H$_{arom}$, C$_q$C$_q$F, m); 162.0 (C$_q$F, d×d, J=259.0 Hz, 4.6 Hz). $^{19}$F-NMR (282 MHz, CDCl$_3$): δ −114.14. $^{31}$P-NMR (121 MHz, CDCl$_3$): δ 19.90. MS (ESI): m/z (%): 509 (2M+H$^+$, 100); 255 (M+H$^+$, 50). IR (cm$^{-1}$) vmax: 1162 (P-OEt); 1628; 1600; 1573; 1509; 2623 (POOH). MP: 80.9-81.3° C. (dioxane). Yield: 83%.

Ethyl 4-bromonapht-1-ylphosphonate: Intermediate 3 Containing a Naphtyl Core with X=Br

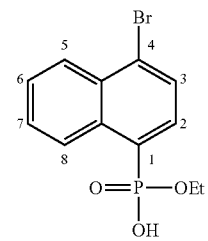 [SMILES: CCOP(=O)(O)c1ccc(Br)c2ccccc12]

The compound is obtained as white crystals in a yield of 91%. $^1$H-NMR (300 MHz, CDCl$_3$): δ 1.22 (3H, t, J=6.9 Hz, CH$_3$); 4.02 (2H, m, CH$_2$); 7.56-7.64 (2H, m, 2×CH$_{arom}$); 7.70 (1H, d×d, J=7.7 Hz, 2.8 Hz, C$_3$H$_{arom}$); 7.93 (1H, d×d, J=16.5 Hz, 7.7 Hz, C$_2$H$_{arom}$); 8.30 (1H, d, J=7.7 Hz, CH$_{arom}$); 8.49 (1H, d, J=9.4 Hz, CH$_{arom}$); 12.42 (1H, s, OH). $^{13}$C-NMR (75 MHz, CDCl$_3$): δ 16.2 (CH$_3$, d, J=5.8 Hz); 62.3 (CH$_2$, d, J=5.8 Hz); 125.2 (C$_q$P, d, J=191.5 Hz); 127.3 (CH$_{arom}$, d, J=4.6 Hz); 127.8 (CH$_{arom}$); 128.0 (CH$_{arom}$); 128.2 (CH$_{arom}$); 128.8 (C$_3$H$_{arom}$, d, J=17.3 Hz); 129.3 (C$_q$Br, d, J=4.6 Hz); 132.1 (C$_q$C$_q$P, d, J=13.9 Hz); 133.6 (C$_2$H$_{arom}$, d, J=10.4 Hz). $^{31}$P-NMR (121 MHz, CDCl$_3$): δ 19.16. MS (ESI): m/z (%): 629/631/633 (2M+H$^+$, 50/100/50); 315/317 (M+H$^+$, 70/70). IR (cm$^{-1}$) vmax: 1162 (P-OEt); 1561; 1503; 1474; 2598 (PO—OH). MP: 125.8-126.5° C. (dioxane). Yield: 91%.

Ethyl napht-1-ylphosphonate: Intermediate 3 Containing a Naphtyl Core with X=H

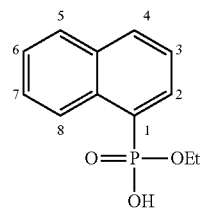

The compound is obtained as an orange oil in a yield of 90%. $^1$H-NMR (300 MHz, CDCl$_3$): δ 1.24 (3H, t, J=7.2 Hz, CH$_3$); 4.06 (2H, m, CH$_2$); 7.43 (1H, t×d, J=7.4 Hz, 3.7 Hz, C$_3$H$_{arom}$); 7.54 (2H, m, 2×CH$_{arom}$); 7.82-7.87 (1H, m, CH$_{arom}$); 7.98 (1H, d, J=8.3 Hz, CH$_{arom}$); 8.51 (1H, d, J=7.7 Hz, CH$_{arom}$); 8.19 (1H, d×d, J=16.5 Hz, 7.4 Hz, C$_2$H$_{arom}$); 10.31 (1H, s, OH). $^{13}$C-NMR (75 MHz, CDCl$_3$): δ 16.3 (CH$_3$, d, J=5.8 Hz); 62.1 (CH$_2$, d, J=5.8 Hz); 124.5 (C$_3$H$_{arom}$, d, J=17.3 Hz); 125.3 (C$_q$P, d, J=190.4 Hz); 126.4 (CH$_{arom}$); 126.9 (CH$_{arom}$, d, J=4.6 Hz); 127.5 (CH$_{arom}$); 128.7 (CH$_{arom}$); 132.7 (C$_q$C$_q$P, d, J=11.5 Hz); 133.3 (CH C$_q$CH, d, J=10.4 Hz); 133.5 (CH$_{arom}$); 133.7 (C$_2$H$_{arom}$, d, J=9.2 Hz). $^{31}$P-NMR (121 MHz, CDCl$_3$): δ 20.96. MS (ESI): m/z (%): 473 (2M+H$^+$, 100), 237 (M+H$^+$, 40). IR (cm$^{-1}$) vmax: 1154 (P-OEt); 1478; 1508; 1572; 1592; 2577 (PO—OH). Yield: 90%.

Ethyl 4-bromophenylphosphonate: Intermediate 3 Containing a Phenyl Core with X=Br

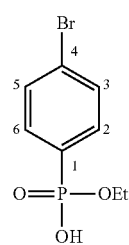

The compound is obtained as a clear oil in a yield of 90%. $^1$H-NMR (300 MHz, CDCl$_3$): δ 1.26 (3H, t, J=7.2 Hz, CH$_3$); 4.02 (2H, ~quin, CH$_2$); 7.53-7.66 (4H, m, 4×CH$_{arom}$); 11.26 (1H, s, OH). $^{13}$C-NMR (75 MHz, CDCl$_3$): δ 16.3 (CH$_3$, d, J=6.9 Hz); 62.3 (CH$_2$, d, J=5.8 Hz); 127.4 (C$_q$Br, d, J=3.5 Hz); 128.0 (C$_q$P, d, J=195.0 Hz); 131.7 (2×CHC$_q$Br, d, J=16.2 Hz); 133.0 (2×CHC$_q$P, d, J=10.4 Hz). $^{31}$P-NMR (121 MHz, CDCl$_3$): δ 19.04. MS (ESI): m/z (%): 529/531/533 (2M+H$^+$, 50/100/50), 265/267 (M+H$^+$, 50/50). IR (cm$^{-1}$) vmax: 1162 (P-OEt); 1648; 1581; 1560; 1479; 2603 (PO—OH). Yield: 90%.

General Procedure for the Conversion of Intermediates 3 to Compounds E and D

In a 25 ml flask 1 equivalent of phosphonic acid is mixed with 10 equivalents of SOCl$_2$. The reaction is placed under inert atmosphere and heated to reflux for a period of 2 hours. After cooling to room temperature, the volatiles are evaporated and the residue is redissolved in 20 ml dry dichloromethane. The inert atmosphere is reinstated and 1 equivalent of amine and 1 equivalent of triethylamine are added at 0° C. The resulting mixture is stirred at room temperature for 16 hours after which it is quenched with 20 ml aqueous saturated NaHCO$_3$. The compound is extracted with three portions of dichloromethane and the combined organic phases are dried (MgSO$_4$) and concentrated.

Ethyl N-(pyridin-2-ylmethyl)-P-(4-fluoronapht-1-yl) phosphonamidate (denominated as 'E2')

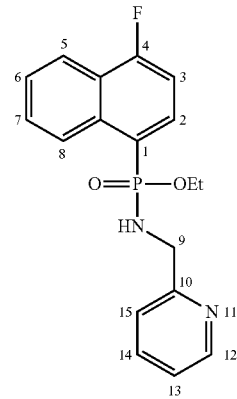 [SMILES: CCOP(=O)(NCc1ccccn1)c1ccc(F)c2ccccc12]

0.5 g phosphonic acid was converted, resulting in the isolation of yellow crystals in 57% yield after column chromatography. $^1$H-NMR (300 MHz, CDCl$_3$): δ 1.34 (3H, q, J=6.8 Hz, CH$_3$); 4.11-4.32 (4H, m, NHCH$_2$, OCH$_2$); 7.06-7.18 (3H, m, 3×CH$_{arom}$); 7.48-7.65 (3H, m, 3×CH$_{arom}$); 8.07-8.18 (2H, m, 2×CH$_{arom}$); 8.44 (1H, m, CH$_{arom}$); 8.68 (1H, d, J=7.7 Hz, CH$_{arom}$). $^{13}$C-NMR (75 MHz, CDCl$_3$): δ 16.5 (CH$_3$, d, J=5.8 Hz); 45.8 (NHCH$_2$); 61.1 (OCH$_2$, d, J=4.6 Hz); 108.5 (C$_2$H$_{arom}$, t, J=17.9 Hz); 121.2 (CH$_{arom}$, d, J=5.8 Hz); 121.6 (CH$_{arom}$); 122.2 (CH$_{arom}$); 123.2 (C$_q$P, d, J=169.6 Hz); 124.0 (C$_q$C$_q$P, d, J=16.2 Hz); 126.6 (CH$_{arom}$); 126.7 (CH$_{arom}$); 128.3 (CH$_{arom}$); 134.3 (C$_3$H$_{arom}$, t, J=8.7 Hz); 134.8 (C$_q$C$_q$F, d×d, J=12.7 Hz, 5.8 Hz); 136.5 (CH$_{arom}$); 149.0 (C$_{12}$H$_{arom}$); 157.7 (CH$_2$C$_q$, d, J=5.8 Hz); 161.7 (C$_q$F, d, J=259.6 Hz). $^{19}$F-NMR (282 MHz, CDCl$_3$): δ 115.36. $^{31}$P-NMR (121 MHz, CDCl$_3$): δ 22.12. MS (ESI): m/z (%): 345 (M+H$^+$, 100). IR (cm$^{-1}$) vmax: 1162 (P-OEt); 1509; 1571; 1594; 1628; 3193 (NH). MP: 58.7-59.5° C. (Et$_3$N). Chromatography: EtOAc/Et$_3$N 95/5 Rf=0.21. Yield: 57%.

Ethyl N-(pyridin-3-ylmethyl)-P-(4-fluoronapht-1-yl) phosphonamidate (Denominated as 'E5')

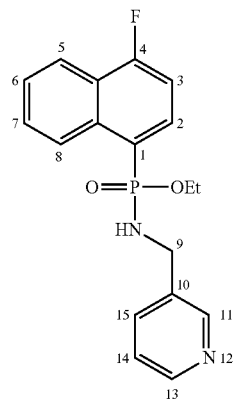 [SMILES: CCOP(=O)(NCc1cccnc1)c1ccc(F)c2ccccc12]

0.3 g phosphonic acid was converted, resulting in the isolation of yellow crystals in 26% yield after column chromatography. $^1$H-NMR (300 MHz, CDCl$_3$): δ 1.33 (3H, t, J=6.9 Hz, CH$_3$); 3.75-3.83 (1H, m, NH); 4.01-4.20 (4H, m, NHCH$_2$, OCH$_2$); 7.10-7.20 (2H, m, 2×CH$_{arom}$); 7.55 (1H, d, J=7.7 Hz, CH$_{arom}$); 7.59-7.66 (2H, m, 2×CH$_{arom}$); 8.08-8.18 (2H, m, 2×CH$_{arom}$); 8.41 (2H, m, 2×CH$_{arom}$); 8.66 (1H, d, J=7.7 Hz, CH$_{arom}$). $^{13}$C-NMR (75 MHz, CDCl$_3$): δ 16.5 (CH$_3$, d, J=6.9 Hz); 42.4 (NHCH$_2$); 61.3 (OCH$_2$, d, J=4.6 Hz); 108.6 (C$_2$Harom, d×d, J=19.6 Hz, 16.2 Hz); 121.4 (CH$_{arom}$, d, J=5.8 Hz); 123.4 (CH$_{arom}$); 123.7 (C$_q$, d, J=4.6 Hz), 124.2 (C$_q$, d×d, J=15.6 Hz, 13.3 Hz); 126.4 (CH$_{arom}$); 126.8 (CH$_{arom}$); 128.5 (CH$_{arom}$); 134.7 (C$_3$H$_{arom}$, t, J=9.2 Hz); 135.1 (C$_q$, d, J=5.8 Hz); 135.4 (CH$_{arom}$); 148.7 (CH$_{arom}$); 149.0 (CH$_{arom}$); 161.9 (C$_q$F, d×d, J=259.6 Hz, 3.5 Hz). $^{19}$FNMR (282 MHz, CDCl$_3$): δ −114.68. $^{31}$P-NMR (121 MHz, CDCl$_3$): δ 21.63. MS (ESI): m/z (%): 345 (M+H$^+$, 100). IR (cm$^{-1}$) vmax: 1164 (P-OEt); 1571; 1579; 1600; 1628; 3192 (NH). MP: 133.6-134.3° C. (Et$_3$N). Chromatography: EtOAc/Et$_3$N 95/5 Rf=0.08. Yield: 26%.

Ethyl N-(benzyl)-P-(4-fluoronapht-1-yl)phosphonamidate (Denominated as 'E6')

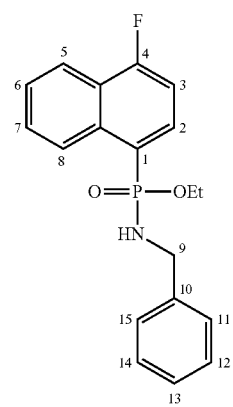 [SMILES: CCOP(=O)(NCc1ccccc1)c1ccc(F)c2ccccc12]

0.5 g phosphonic acid was converted, resulting in the isolation of yellow crystals in 46% yield after column chromatography. $^1$H-NMR (300 MHz, CDCl$_3$): δ 1.35 (3H, t, J=6.9 Hz, CH$_3$); 3.14-3.22 (1H, m, NH); 4.02-4.23 (4H, m, NHCH$_2$, OCH$_2$); 7.14-7.28 (6H, m, 6×CH$_{arom}$); 8.10-8.20 (2H, m, 2×CH$_{arom}$); 7.63 (2H, m, 2×CH$_{arom}$); 8.70 (1H, d, J=7.7 Hz, CH$_{arom}$). $^{13}$CNMR (75 MHz, CDCl$_3$): δ 16.5 (CH$_3$, d, J=6.9 Hz); 44.9 (NHCH$_2$); 61.0 (OCH$_2$, d, J=5.8 Hz); 108.5 (C$_2$H$_{arom}$, d×d, J=19.6 Hz, 17.3 Hz); 121.3 (CH$_{arom}$, d, J=3.5 Hz); 123.1 (C$_q$P, d, J=171.9 Hz); 124.2 (C$_q$C$_q$P, t, J=14.4 Hz); 126.7 (2×CH$_{arom}$); 127.3 (CH$_{arom}$, d, J=4.6 Hz); 127.5 (2×CH$_{arom}$); 128.4 (CH$_{arom}$); 128.5 (2×CH$_{arom}$, d, J=3.5 Hz); 134.5 (C$_3$H$_{arom}$, d, J=8.1 Hz); 134.8 (C$_q$C$_q$F, d×d, J=13.3 Hz, 4.0 Hz); 139.7 (CH$_2$C$_q$); 161.8 (C$_q$F, d×d, J=255.6 Hz, 4.0 Hz). $^{19}$F-NMR (282 MHz, CDCl$_3$): δ −115.08. $^{31}$PNMR (121 MHz, CDCl$_3$): δ 22.05. MS (ESI): m/z (%): 344 (M+H$^+$, 100), 687 (2M+H$^+$, 90). IR (cm$^{-1}$) vmax: 1508; 1571; 1601; 1628; 3187 (NH). MP: 120.1-120.8° C. (Et$_3$N). Chromatography: EtOAc/hexanes 60/40+5% Et$_3$N Rf=0.24. Yield: 46%.

Ethyl N-(pyridin-2-ylmethyl)-P-(4-bromonapht-1-yl) phosphonamidate (denominated as 'E1')

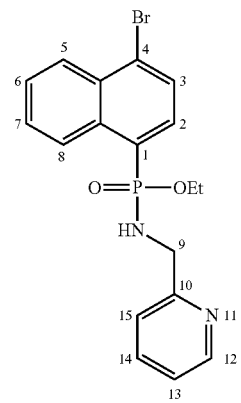

0.5 g phosphonic acid was converted, resulting in the isolation of yellow crystals in 62% yield after column chromatography. $^1$H-NMR (300 MHz, CDCl$_3$): δ 1.35 (3H, t, J=7.2 Hz, CH$_3$); 4.29-4.11 (4H, m, NHCH$_2$, OCH$_2$); 7.10 (1H, d, J=7.2 Hz, CH$_{arom}$); 7.12 (1H, d, J=7.7 Hz, CH$_{arom}$); 7.54 (1H, t×d, J=7.7 Hz, 1.7 Hz, CH$_{arom}$); 7.63 (2H, m, 2×CH$_{arom}$); 7.81 (1H, d×d, J=7.7 Hz, 2.8 Hz, C$_3$H$_{arom}$); 7.99 (1H, d×d, J=15.4 Hz, 7.7 Hz, C$_2$H$_{arom}$); 8.32 (1H, d×t, J=7.2 Hz, 2.8 Hz, CH$_{arom}$); 8.45 (1H, d×t, J=4.4 Hz, 1.7 Hz, CH$_{arom}$); 8.72-8.69 (1H, m, CH$_{arom}$). $^{13}$C-NMR (75 MHz, CDCl$_3$): δ 16.5 (CH$_3$, d, J=5.8 Hz); 45.8 (NHCH$_2$); 61.1 (OCH$_2$, d, J=5.8 Hz); 121.6 (CH$_{arom}$); 122.2 (CH$_{arom}$); 127.5 (C$_q$P, d, J=170.8 Hz); 127.3 (CH$_{arom}$, d, J=4.6 Hz); 127.7 (CH$_{arom}$); 128.0 (CH$_{arom}$); 128.1 (CH$_{arom}$); 128.9 (C$_3$H$_{arom}$, d, J=15.0 Hz); 132.2 (C$_q$C$_q$P, d, J, 12.7 Hz); 133.4 (C$_2$H$_{arom}$, d, J=8.1 Hz); 134.0 (C$_q$C$_q$Br, d, J=12.7 Hz); 136.5 (CH$_{arom}$); 148.9 (C$_{12}$H$_{arom}$); 157.6 (CH$_2$C$_q$). $^{31}$P-NMR (121 MHz, CDCl$_3$): δ 22.08. MS (ESI): m/z (%): 405/407 (M+H$^+$, 100/100). IR (cm$^{-1}$) vmax: 1159 (P-OEt); 1474; 1501; 1560; 1589; 3188 (NH). MP: 87.6-88.4° C. (Et$_3$N). Chromatography: EtOAc/Et$_3$N 95/5 Rf=0.15. Yield: 62%.

Ethyl N-(pyridin-3-ylmethyl)-P-(4-bromonapht-1-yl)phosphonamidate (denominated as 'E3')

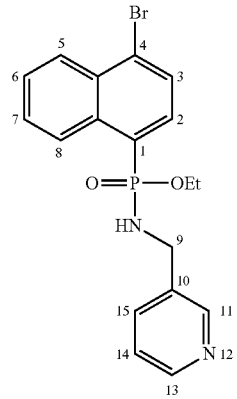 [SMILES: CCOP(=O)(NCc1cccnc1)c1ccc(Br)c2ccccc12]

0.5 g phosphonic acid was converted, resulting in the isolation of brownish crystals in 57% yield after crystallisation from dichloromethane/hexanes and column chromatography of the mother liquor. $^1$H-NMR (300 MHz, CDCl$_3$): δ 1.32 (3H, t, J=7.2 Hz, CH$_3$); 3.85 (1H, ~q, J=7.7 Hz, NH); 4.00-4.09 (2H, m, NHCH$_2$); 4.13 (2H, ~quin, OCH$_2$); 7.12 (1H, dxd, J=7.7 Hz, 5.0 Hz, CH$_{arom}$); 7.53 (1H, d, J=7.7 Hz, CH$_{arom}$); 7.58-7.67 (2H, m, 2×CH$_{arom}$); 7.82 (1H, dxd, J=7.7 Hz, 2.8 Hz, C$_3$H$_{arom}$); 7.97 (1H, dxd, J=15.4 Hz, 7.7 Hz, C$_2$H$_{arom}$); 8.33 (1H, m, CH$_{arom}$); 8.41 (2H, br. s, 2×CH$_{arom}$); 8.67 (1H, d, J=7.7 Hz, CH$_{arom}$). $^{13}$C-NMR (75 MHz, CDCl$_3$): δ 16.5 (CH$_3$, d, J=6.9 Hz); 42.4 (NHCH$_2$); 61.4 (OCH$_2$, d, J=4.6 Hz); 123.4 (CH$_{arom}$); 125.6 (C$_q$); 126.9 (CH$_{arom}$, d, J=4.6 Hz); 127.9 (2×CH$_{arom}$); 128.3 (CH$_{arom}$, d, J=6.9 Hz); 129.0 (C$_3$H$_{arom}$, d, J=16.2 Hz); 129.2 (C$_q$); 132.3 (C$_q$, d, J=12.7 Hz); 133.8 (C$_2$H$_{arom}$, d, J=9.2 Hz); 133.9 (C$_q$); 135.1 (C$_q$, d, J=5.8 Hz); 135.5 (CH$_{arom}$); 148.6 (CH$_{arom}$); 148.8 (CH$_{arom}$). $^{31}$P-NMR (121 MHz, CDCl$_3$): δ 21.44. MS (ESI): m/z (%): 405/407 (M+H$^+$, 100/100). IR (cm$^{-1}$) vmax: 1163 (P-OEt); 1478; 1500; 1560; 1579; 3187 (NH). MP: 105.6-106.4° C. (Et$_3$N). Chromatography: EtOAc/Et$_3$N 95/5 Rf=0.11. Yield: 57%.

Ethyl N-(pyridin-4-ylmethyl)-P-(4-bromonapht-1-yl)phosphonamidate (denominated as 'E7')

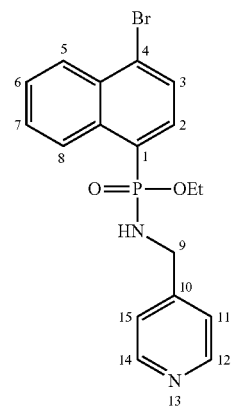 [SMILES: CCOP(=O)(NCc1ccncc1)c1ccc(Br)c2ccccc12]

0.5 g phosphonic acid was converted, resulting in the isolation of white crystals in 8% yield after column chromatography. $^1$H-NMR (300 MHz, CDCl$_3$): δ 1.34 (3H, t, J=6.9 Hz, CH$_3$); 3.80 (1H, ~q, J=8.3 Hz, NH); 4.05-4.15 (2H, m, NHCH$_2$); 4.16 (2H, ~quin, J=7.3 Hz, OCH$_2$); 7.14 (2H, d, J=5.5 Hz, 2×CH$_{arom}$) 7.60-7.69 (2H, m, 2×CH$_{arom}$) 7.83 (1H, dxd, J=7.7 Hz, 3.3 Hz, C$_3$H$_{arom}$); 7.98 (1H, dxd, J=15.4 Hz, 7.7 Hz, C$_2$H$_{arom}$); 8.35 (1H, m, CH$_{arom}$); 8.43 (2H, br. s, 2×CH$_{arom}$) 8.68 (1H, d, J=6.9 Hz, CH$_{arom}$). $^{13}$C-NMR (75 MHz, CDCl$_3$): δ 16.5 (CH$_3$, d, J=6.9 Hz); 43.8 (NHCH$_2$); 61.6 (OCH$_2$, d, J=5.8 Hz); 122.2 (2×CH$_{arom}$); 126.7 (C$_q$P, d, J=169.6 Hz); 126.9 (CH$_{arom}$, d, J=4.6 Hz); 127.9 (2×CH$_{arom}$); 128.3 (CH$_{arom}$, d, J=2.3 Hz); 129.0 (C$_3$H$_{arom}$, d, J=15.0 Hz); 129.3 (C$_q$Br, d, J=3.5 Hz); 132.3 (C$_q$C$_q$P, d, J=12.7 Hz); 133.8 (C$_2$H$_{arom}$, d, J=9.2 Hz); 133.9 (C$_q$C$_q$Br, d, J=12.7 Hz); 148.7 (CH$_2$C$_q$); 149.8 (2×CH$_{arom}$). $^{31}$P-NMR (121 MHz, CDCl$_3$): δ 21.84. MS (ESI): m/z (%): 405/407 (M+H$^+$, 100/100). IR (cm$^{-1}$) vmax: 1162 (P-OEt); 1463; 1501; 1561; 1600; 3161 (NH). MP: 131.8-132.5° C. (Et$_3$N). Chromatography: EtOAc/Et$_3$N 95/5 Rf=0.10. Yield: 8%.

Ethyl N-(benzyl)-P-(4-bromonapht-1-yl)phosphonamidate (Denominated as 'E4')

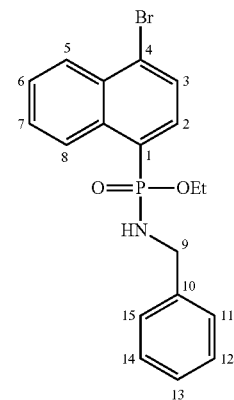 [SMILES: CCOP(=O)(NCc1ccccc1)c1ccc(Br)c2ccccc12]

0.5 g phosphonic acid was converted, resulting in the isolation of white crystals in 50% yield after crystallisation from dichloromethane/hexanes and column chromatography of the mother liquor. $^1$H-NMR (300 MHz, CDCl$_3$): δ 1.34 (3H, t, J=6.9 Hz, CH$_3$); 3.32 (1H, ~q, J=7.7 Hz, NH); 4.00-4.10 (2H, m, NHCH$_2$); 4.17 (2H, quintet, J=7.2 Hz, OCH$_2$); 7.17-7.25 (5H, m, 5×CH$_{arom}$); 7.60-7.68 (2H, m, 2×CH$_{arom}$); 7.82 (1H, dxd, J=7.7 Hz, 2.8 Hz, CH$_{arom}$); 7.99 (1H, dxd, J=14.9 Hz, 7.7 Hz, C$_2$H$_{arom}$); 8.34 (1H, m, CH$_{arom}$); 8.70-8.73 (1H, m, CH$_{arom}$). $^{13}$C-NMR (75 MHz, CDCl$_3$): δ 16.5 (CH$_3$, d, J=6.9 Hz); 45.0 (NHCH$_2$); 61.3 (OCH$_2$, d, J=5.8 Hz); 126.8 (C$_q$P, d, J=128.1 Hz); 127.1 (CH$_{arom}$, d, J=4.6 Hz); 127.4 (CH$_{arom}$); 127.5 (2×CH$_{arom}$); 127.8 (CH$_{arom}$); 128.2 (CH$_{arom}$, d, J=4.6 Hz); 128.6 (3×CH$_{arom}$); 129.0 (CH$_{arom}$, d, J=15.0 Hz); 129.0 (C$_q$Br, d, J=4.6 Hz); 132.3 (C$_q$C$_q$P, d, J=12.7 Hz); 133.8 (CH$_{arom}$, d, J=8.1 Hz); 134.0 (C$_q$C$_q$Br, d, J=11.5 Hz); 139.4 (CH$_2$C$_q$, d, J=6.9 Hz). $^{31}$P-NMR (121 MHz, CDCl$_3$): δ 21.37. MS (ESI): m/z (%): 404/406 (M+H$^+$, 100/100). IR (cm$^{-1}$) vmax: 1159 (P-OEt); 1451; 1500; 1560; 3196 (NH). MP: 135.8-136.7° C. (Et$_3$N). Chromatography: EtOAc/hexanes 60/40+5% Et$_3$N Rf=0.21. Yield: 50%.

Ethyl N-(pyridin-2-ylmethyl)-P-(napht-1-yl)phosphonamidate (Denominated as 'E9')

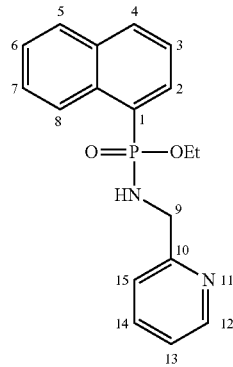 [SMILES: CCOP(=O)(NCc1ccccn1)c1cccc2ccccc12]

0.5 g phosphonic acid was converted, resulting in the isolation of an orange oil in 25% yield after column chromatography. $^1$H-NMR (300 MHz, CDCl$_3$): δ 1.33 (3H, t, J=7.2 Hz, OCH$_2$C$\underline{H}$$_3$); 4.17 (2H, qxd, J$^1$=J$^2$=7.2 Hz, OC$\underline{H}$$_2$CH$_3$); 4.27 (2H, ~dxd, J$^1$=8.8 Hz, J$^2$=6.1 Hz, C$\underline{H}$$_2$NH); 4.39 (1H, br. s, NH); 7.07 (1H, dxd, J$^1$=7.2 Hz, J$^2$=5.0 Hz, C$_{13}$H$_{arom}$); 7.15 (1H, d, J=7.7 Hz, C$_{15}$H$_{arom}$); 7.43-7.58 (4H, m, 4×CH$_{arom}$); 7.84 (1H, d, J=7.7 Hz, CH$_{arom}$); 7.96 (1H, d, J=7.7 Hz, CH$_{arom}$); 8.15 (1H, dxdxd, J$^1$=15.7 Hz, J$^2$=7.2 Hz, J$^3$=1.1 Hz, CH$_{arom}$); 8.42 (1H, d, J=5.0 Hz, C$_{12}$H$_{arom}$); 8.69 (1H, d, J=8.8 Hz, CH$_{arom}$). $^{13}$C-NMR (75 MHz, CDCl$_3$): δ 16.5 (OCH$_2$$\underline{C}$H$_3$, d, J=6.9 Hz); 45.8 (CH$_2$NH); 61.0 (O$\underline{C}$H$_2$CH$_3$, d, J=5.8 Hz); 121.7 (C$_{15}$H$_{arom}$); 122.2 (C$_{13}$H$_{arom}$); 124.6 (CH$_{arom}$, d, J=16.2 Hz); 126.3 (CH$_{arom}$); 126.7 (CH$_{arom}$, d, J=4.6 Hz); 127.1 (C$_q$P, d, J=168.5 Hz); 127.3 (CH$_{arom}$); 128.8 (CH$_{arom}$); 132.9 (C$_q$, d, J=10.4 Hz); 133.1 (CH$_{arom}$, d, J=3.5 Hz); 133.5 (CH$_{arom}$, d, J=8.1 Hz); 133.7 (C$_q$, d, J=11.5 Hz); 136.6 (CH$_{arom}$); 148.9 (C$_{12}$H$_{arom}$); 157.9 (C$_q$N, d, J=5.8 Hz). $^{31}$P-NMR (121 MHz, CDCl$_3$): δ 22.95. MS (ESI): m/z (%): 327 (M+H$^+$, 100). HRMS (ESI): calcd. for C$_{18}$H$_{20}$N$_2$O$_2$P: 327, 1257 (M+H$^+$). found: 327, 1260 (M+H$^+$). IR (cm$^{-1}$) νmax: 1199 (P=O); 1435; 1591; 3192 (NH). Chromatography: EtOAc/hexanes 90/10 Rf=0.14. Yield: 25%.

Ethyl N-(pyridin-2-ylmethyl)-P-(4-bromophenyl)phosphonamidate (Denominated as 'E8')

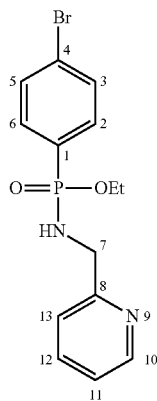 [SMILES: CCOP(=O)(NCc1ccccn1)c1ccc(Br)cc1]

0.3 g phosphonic acid was converted, resulting in the isolation of an orange oil in 16% yield after column chromatography. $^1$H-NMR (300 MHz, CDCl$_3$): δ 1.23 (3H, t, J=7.2 Hz, CH$_3$); 4.01 (2H, quinxd, J=7.2 Hz, 2.2 Hz, OCH$_2$); 4.11 (2H, dxd, J=9.4 Hz, 6.4 Hz, NHC$\underline{H}$$_2$); 4.33 (1H, dxt, J=9.9 Hz, 6.4 Hz, NH); 7.08 (1H, dxd, J=7.6 Hz, 4.9 Hz, C$_{11}$H$_{arom}$); 7.13 (1H, d, J=7.6 Hz, C$_9$H$_{arom}$); 7.46 (2H, dxd, J=8.3 Hz, 3.3 Hz, 2×CHC$_q$Br); 7.53 (1H, txd, J=7.6 Hz, 1.7 Hz, C$_{12}$H$_{arom}$); 7.57 (2H, dxd, J=12.7 Hz, 8.3 Hz, 2×CHC$_q$P); 8.41 (1H, d, J=4.9 Hz, C$_{10}$H$_{arom}$). $^{13}$C-NMR (75 MHz, CDCl$_3$): δ 16.4 (CH$_3$, d, J=6.9 Hz); 45.7 (NHCH$_2$); 60.9 (OCH$_2$, d, J=5.8 Hz); 121.6 (CH$_{arom}$); 122.3 (CH$_{arom}$); 126.8 (C$_q$Br, d, J=3.5 Hz); 130.1 (C$_q$P, d, J=175.4 Hz); 131.7 (2×$\underline{C}$HC$_q$Br, d, J=15.0 Hz); 133.1 (2×$\underline{C}$HC$_q$P, d, J=11.5 Hz); 136.7 (C$_{12}$H$_{arom}$); 149.0 (C$_{10}$H$_{arom}$); 157.7 (CH$_2$$\underline{C}$$_q$, d, J=6.9 Hz). $^{31}$P-NMR (121 MHz, CDCl$_3$): δ 22.35. MS (ESI): m/z (%): 355/357 (M+H$^+$, 100/100). IR (cm$^{-1}$) νmax: 1163 (P-OEt); 1475; 1579; 1592; 3204 (NH). Chromatography: EtOAc/Et$_3$N 95/5 Rf=0.16. Yield: 16%

Ethyl N-(pyridin-2-ylmethyl)-P-(phenyl)phosphonamidate (Denominated as 'D1')

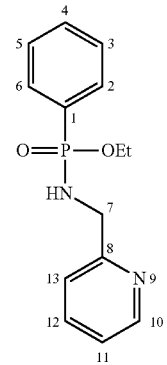

0.5 g phosphonic acid was converted, resulting in the isolation of an orange oil in 78% yield. No purification step was needed. $^1$H-NMR (300 MHz, CDCl$_3$): δ 1.33 (3H, t, J=7.2 Hz, OCH$_2$CH$_3$); 3.97 (1H, ~br. s, NH); 4.12 (2H, qxd, J$^1$=J$^2$=7.2 Hz, OCH$_2$); 4.23 (2H, dxd, J$^1$=8.5 Hz, J$^2$=6.3 Hz, CH$_2$NH); 7.17 (1H, dxd, J$^1$=7.5 Hz, J$^2$=5.0 Hz, C$_{11}$H$_{arom}$); 7.22 (1H, d, J=7.5 Hz, C$_{13}$H$_{arom}$); 7.39-7.54 (3H, m, 3×CH$_{arom}$); 7.62 (1H, txd, J$^1$=7.5 Hz, J$^2$=1.7 Hz, C$_{12}$H$_{arom}$); 7.77-7.86 (2H, m, C$_{2,6}$H$_{arom}$); 8.52 (1H, ~d, J=5.0 Hz, C$_{10}$H$_{arom}$). $^{13}$C-NMR (75 MHz, CDCl$_3$): δ 16.5 (CH$_3$, d, J=6.9 Hz); 45.8 (CH$_2$NH); 60.8 (OCH$_2$, d, J=5.8 Hz); 121.6 (C$_{13}$H$_{arom}$); 122.3 (C$_{11}$H$_{arom}$); 128.4 (2×CH$_{arom}$, d, J=13.9 Hz); 130.9 (C$_q$P, d, J=173.0 Hz); 131.5 (2×CH$_{arom}$, d, J=10.4 Hz); 131.8 (CH$_{arom}$, d, J=2.3 Hz); 136.7 (C$_{12}$H$_{arom}$); 149 (C$_{10}$H$_{arom}$); 157.9 (C$_q$N, d, J=6.9 Hz). $^{31}$P-NMR (121 MHz, CDCl$_3$): δ 23, 33. MS (ESI): m/z (%): 277 (M+H$^+$, 100). HRMS (ESI): calcd. for C$_{14}$H$_{18}$N$_2$O$_2$P: 277, 1100 (M+H$^+$). found: 277, 1104 (M+H$^+$). IR (cm$^{-1}$) νmax: 1207 (P=O); 1437; 1591; 3200 (NH). Chromatography: EtOAc Rf=0.13. Yield: 78%.

Ethyl N-(pyridin-3-yl)-P-(phenyl)phosphonamidate (Denominated as 'D3')

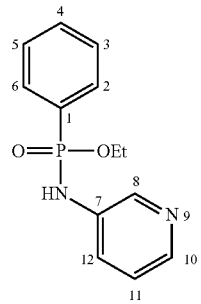

0.5 g phosphonic acid was converted, resulting in the isolation of a yellow oil in 75% yield after column chromatography. $^1$H-NMR (300 MHz, CDCl$_3$): δ 1.39 (3H, t, J=7.2 Hz, CH$_3$); 4.13-4.37 (2H, m, OCH$_2$); 6.46 (1H, ~d, J=5.5 Hz, NH); 7.08 (1H, dxd, J$^1$=8.3 Hz, J$^2$=4.5 Hz, C$_{11}$H$_{arom}$); 7.33-7.38 (1H, m, C$_{12}$H$_{arom}$); 7.41-7.48 (2H, m, 2×CH$_{arom}$); 7.51-7.57 (1H, m, CH$_{arom}$); 7.81-7.89 (2H, m, C$_{2,6}$H$_{arom}$); 8.15 (1H, dxd, J$^1$=4.5 Hz, J$^2$=1.4 Hz, C$_{10}$H$_{arom}$); 8.30 (1H, d, J=2.8 Hz, C$_8$H$_{arom}$). $^{13}$C-NMR (75 MHz, CDCl$_3$): δ 16.3 (CH$_3$, d, J=6.9 Hz); 61.2 (OCH$_2$, d, J=5.8 Hz); 123.7 (C$_{11}$H$_{arom}$); 124.4 (C$_{12}$H$_{arom}$, d, J=5.8 Hz); 128.6 (2×CH$_{arom}$, d, J=15.0 Hz); 129.8 (C$_q$P, d, J=176.5 Hz); 131.3 (C$_{2,6}$H$_{arom}$, d, J=10.4 Hz); 132.4 (CH$_{arom}$, d, J=2.3 Hz); 137.9 (C$_q$NH); 139.7 (C$_8$H$_{arom}$, d, J=8.1 Hz); 142.1 (C$_{10}$H$_{arom}$). $^{31}$P-NMR (121 MHz, CDCl$_3$): δ 17.62. MS (ESI): m/z (%): 263 (M+H$^+$, 100). HRMS (ESI): calcd for C$_{13}$H$_{16}$N$_2$O$_2$P: 263, 0944 (M+H$^+$). found: 263,0951 (M+H$^+$). IR (cm$^{-1}$) vmax: 1212 (P=O); 1472; 1586; 3396 (NH). Chromatography: EtOAc/hexanes 90/10 Rf=0.14. Yield: 75%.

Ethyl (pyridin-2-ylmethyl) phenylphosphonate (Denominated as 'D2')

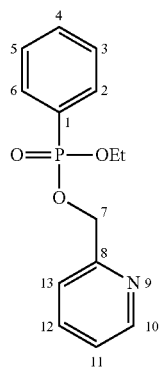 [SMILES: CCOP(=O)(OCc1ccccn1)c1ccccc1]

0.5 g phosphonic acid was converted, resulting in the isolation of a brown oil in 56% yield after column chromatography. $^1$H-NMR (300 MHz, CDCl$_3$): δ 1.34 (3H, t, J=7.2 Hz, CH$_3$); 4.10-4.27 (2H, m, OCH$_2$); 5.15 (1H, dxd, J$^1$=13.2 Hz, J$^2$=7.7 Hz, OCH$_a$H$_b$C$_q$); 5.21 (1H, dxd, J$^1$=13.2 Hz, J$^2$=7.7 Hz, OCH$_a$H$_b$C$_q$); 7.21 (1H, ~dxd, J$^1$=7.2 Hz, J$^2$=4.8 Hz, C$_{11}$H$_{arom}$); 7.44-7.50 (3H, m, 2×CH$_{arom}$, C$_{13}$H$_{arom}$); 7.54-7.61 (1H, m, CH$_{arom}$); 7.70 (1H, txd, J$^1$=7.2 Hz, J$^2$=1.5 Hz, C$_{12}$H$_{arom}$); 7.82-7.90 (2H, m, C$_{2,6}$H$_{arom}$); 8.55 (1H, ~dxd, J$^1$=4.8 Hz, J$^2$=1.5 Hz, C$_{10}$H$_{arom}$). $^{13}$C-NMR (75 MHz, CDCl$_3$): δ 16.2 (CH$_3$, d, J=6.9 Hz); 62.4 (OCH$_2$CH$_3$, d, J=5.8 Hz); 67.7 (OCH$_2$C$_q$, d, J=5.8 Hz); 121.3 (C$_{13}$H$_{arom}$); 122.8 (C$_{11}$H$_{arom}$); 127.6 (C$_q$P, d, J=189.2 Hz); 128.5 (2×CH$_{arom}$, d, J=15.0 Hz); 131.7 (C$_{2,6}$H$_{arom}$, d, J=9.2 Hz); 132.6 (CH$_{arom}$, d, J=2.3 Hz); 136.8 (C$_{12}$H$_{arom}$); 149.0 (CmH$_{arom}$); 156.1 (C$_q$N, d, J=8.1 Hz). $^{31}$P-NMR (121 MHz, CDCl$_3$): δ 20.00. MS (ESI): m/z (%): 278 (M+H$^+$, 100). HRMS (ESI): calcd for C$_{14}$H$_{17}$NO$_3$P: 278, 0941 (M+H$^+$). found: 278, 0946 (M+H$^+$). IR (cm$^{-1}$) vmax: 1248 (P=O); 1438; 1592; 3453 (NH). Chromatography: EtOAc/hexanes 60/40 Rf=0.23. Yield: 56%.

Synthesis of Hydrogen N-(pyridin-2-ylmethyl)-P-(4-bromonapht-1-yl)phosphonamidate (Denominated as 'E10')

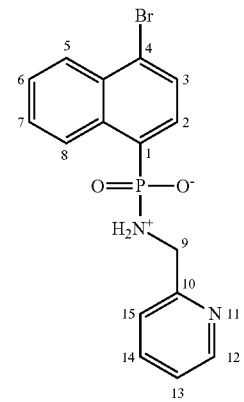 [SMILES: O=P([O-])([NH2+]Cc1ccccn1)c1ccc(Br)c2ccccc12]

In a 50 ml flask, 0.5 g Ethyl N-(pyridin-2-ylmethyl)-P-(4-bromonapht-1-yl)phosphonamidate was dissolved in 20 ml of a 1/1 mixture of MeOH and 1.5M aqueous LiOH. The mixture was heated to reflux for 45 minutes and cooled to room temperature. After washing with chloroform (3×15 ml), the pH was adjusted to 1, using concentrated HCl (12M). Extraction using chloroform delivered zwitterionic E10, in a yield of 42% and 70% purity by HPLC. Attempt to increase purity by crystallisation or ion exchange chromatography have failed.

Plant Material

*Arabidopsis thaliana* Columbia (Col0) seedlings were grown in square 12×12 cm petriplates (Gosselin, BP124-04) on 50 mL of basal medium containing 1.5 g/L MS basal salts (Duchefa, M0221.0050), 5.0 g/L D-sucrose, 0.5 g/L MES (Duchefa, M1503.0100) and 8.0 g/L agar (MC29, Amersham), pH5.7. Seeds were 4 h surface-sterilised in chlorine gas (100 mL commercial bleach and 3 mL hypochloric acid in a bell jar), spread on petriplates and stratified for 4 d in the dark at 5° C. followed by 8 hours in the light (70 µmol/m$^2$s) at 25° C. to stimulate germination. Thereupon, the plates are covered in aluminium foil for 3 days to induce etiolation and skotomorphogenic growth with hypocotyls of 60 to 100 mm long. The etiolated seedlings were transferred to the growth room (25° C., 70 µmol/m$^2$s, 16 h light/8 h dark) and subjected to different treatments for 10 days.

2. Plant Growth Regulators and Pyrabactin Analogues

Abscisic acid and pyrabactin were purchased by Sigma Aldrich (B190923.27 and B3438) and dissolved in DMSO to prepare a 10 mM stock. The self-synthesised phosphonamide analogues were similarly dissolved in DMSO. For germination assays seedlings were incubated on medium containing growth regulators. For root and shoot growth assays, plantlets were pre-grown on K1 medium and transferred to medium containing growth regulators. Stomatal aperture assays were performed by adding growth regulators directly to the cells under observation.

3. Root Phenotypic Analysis

Root phenotypes were scored using a binocular microscope (Olympus, SZX9). Overview pictures were taken with a Nikon D5000 camera and images were analysed with ImageJ® software. The primary root length was measured for individual seedlings via the Segmented Line tool, in which an estimated profile of the root is tracked and the length of this profile is calculated.

4. Statistical Analysis

The counted and measured root data are represented in graphs showing the values and the statistical error bars. Further statistical analysis to determine significance between the different treatments is performed in S-Plus (version 8, TIBCO Software Inc.). To check the normality of the data and distribution of the variances (homoscedasticity) respectively a Kolmogorov-Smirnov and a Modified Levene test were applied. In the datasets fulfilling normality and homoscedasticity, Anova tests were continued to compare the treatments. The Bonferroni-method was used to compare multiple averages. More frequently, a non-parametric Wilcoxon Rank test compares the averages two by two. Graph bars receiving the same letter code are not significantly different. Different letters indicate significantly different averages between the treatments.

Results In addition to the below mentioned effect of phosphonamide pyrabactin analogues on root development, the effect of the analogues in typical ABA-related biological processes, such as seed germination and stomatal closure, are described further Effect of Pyrabactin and Phosphonamide Analogues on Primary Root Growth Previous experiments have shown that 10 µM pyrabactin and ABA cause significant reductions in primary root length. Hence, we initially evaluated the effect of pyrabactin analogues at this concentration.

As expected, 10 µM ABA and pyrabactin reduced the primary root length by 5- and 2.5-fold respectively (FIG. 1). Pyrabactin analogues E4 and E7 strongly inhibited primary root growth, whereas E1, E5, E9 and E10 were modest inhibitors of primary root elongation. Analogue E6 was the only compound reducing the root growth comparable to pyrabactin. The other pyrabactin analogues E2, E3, D1, D2 and D3 did not show a significant effect. Remarkably, compound E8 showed a slight, but significant increase in primary root length (FIG. 1).

Pyrabactin and Phosphonamide Analogues Involved in Lateral Root Development

Figure 2:
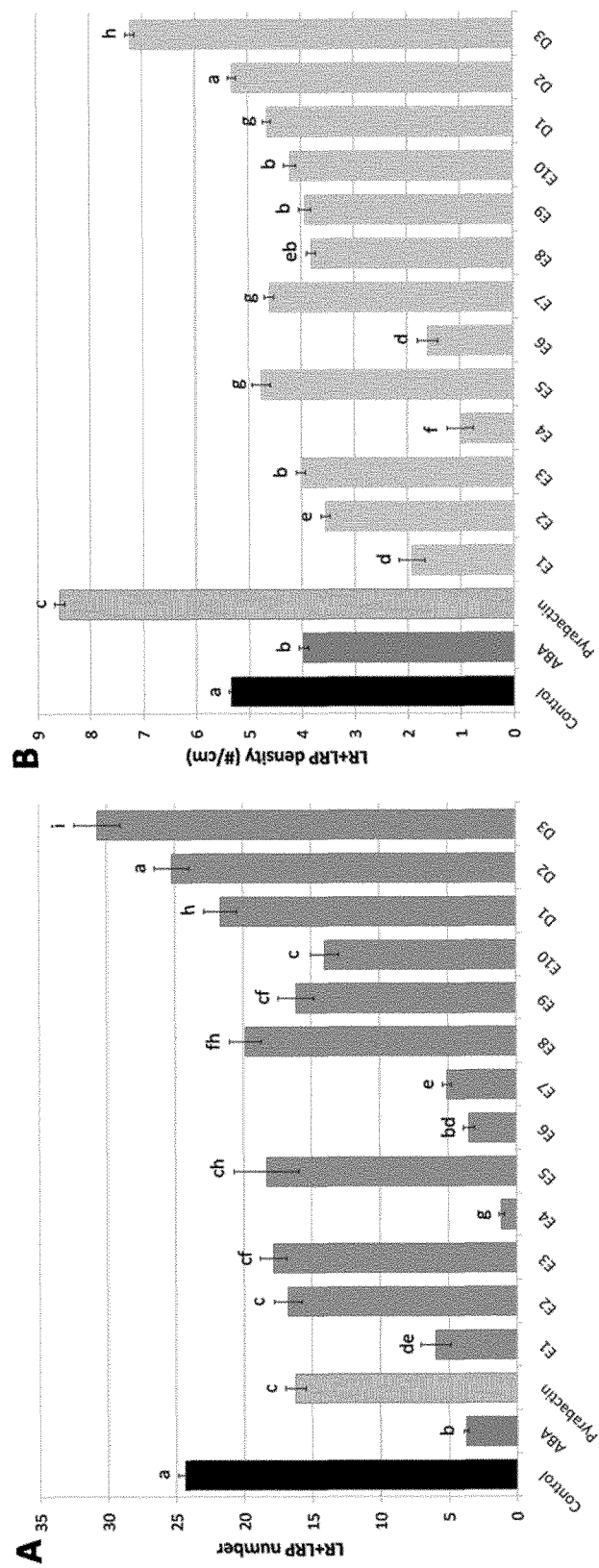
FIG. 2: ABA, pyrabactin and the different pyrabactin analogues differentially affect lateral root initiation, (A) represented as the sum of the emerged lateral roots (LR) and the lateral root primordia (LRP) or as density values (#/cm primary root) (B).

Branching of the primary root is an important determinant of root architecture and is controlled by ABA-signalling, which has a regulatory function during the onset and emergence of lateral roots and translates environmental signals into organogenic responses (De Smet et al, 2003; De Smet et al, 2006; Guo et al, 2009; Guo et al, 2012; Signora et al, 2001). We therefore analysed the number of lateral root primordia (LRP) and lateral roots (LR) upon hormone treatment. FIG. 2 A shows the total number of primordia and emerged roots appearing on the primary root of 13 d old, etiolated *Arabidopsis thaliana* seedlings. ABA strongly reduced the number of LR+ LRP, while pyrabactin only did moderately affect lateral root initiation (FIG. 2 B). Analogues E1, E4, E6 and E7 were strong inhibitors, whereas E2, E3, E5, E8, E9, E10 and D1 were modest to weak inhibitors of lateral root formation. Analogue D2 did not have a significant effect and D3 enhanced lateral root induction (FIG. 2 A). Moreover, when considering density values, ABA-treatment reduced the number of roots per cm primary root. Pyrabactin on the other hand significantly increased the LR+ LRP density (FIG. 2 B). Treatment with analogues E1, E4 and E6 resulted in a strong density reduction (even stronger than ABA). Analogue E7, affected both the lateral root numbers and the primary root length, resulting in normal density values of around 5 LR+ LRP per cm primary root. E2, E3, E8, E9, E10 and D1 reduced the numbers of LR+ LRP similarly to ABA. Whereas analogue D2 did not significantly affect the LR numbers, D3 treatment increased the LR density (FIG. 2 B).

The opposing effects of ABA and pyrabactin on lateral root density as well as the variable effects of the pyrabactin analogues lend support for the hypothesis that the regulation of lateral root formation follows a complex path, including inhibitory as well as stimulatory ABA signalling.

The Effect of Phosphonamide Analogues on Adventitious Root Organogenesis

The root system may also consist of shoot-borne or adventitious roots (AR) which appear on the hypocotyls of etiolated *Arabidopsis* seedlings. The fact that ARs are influenced by the water status indicates a possible role of ABA or related molecules during AR formation. To determine the effect of ABA and related compounds, we scored AR formation on treated seedlings. Since the hypocotyl length of the seedlings is not affected by the analogues no density correction was required.

Figure 3:
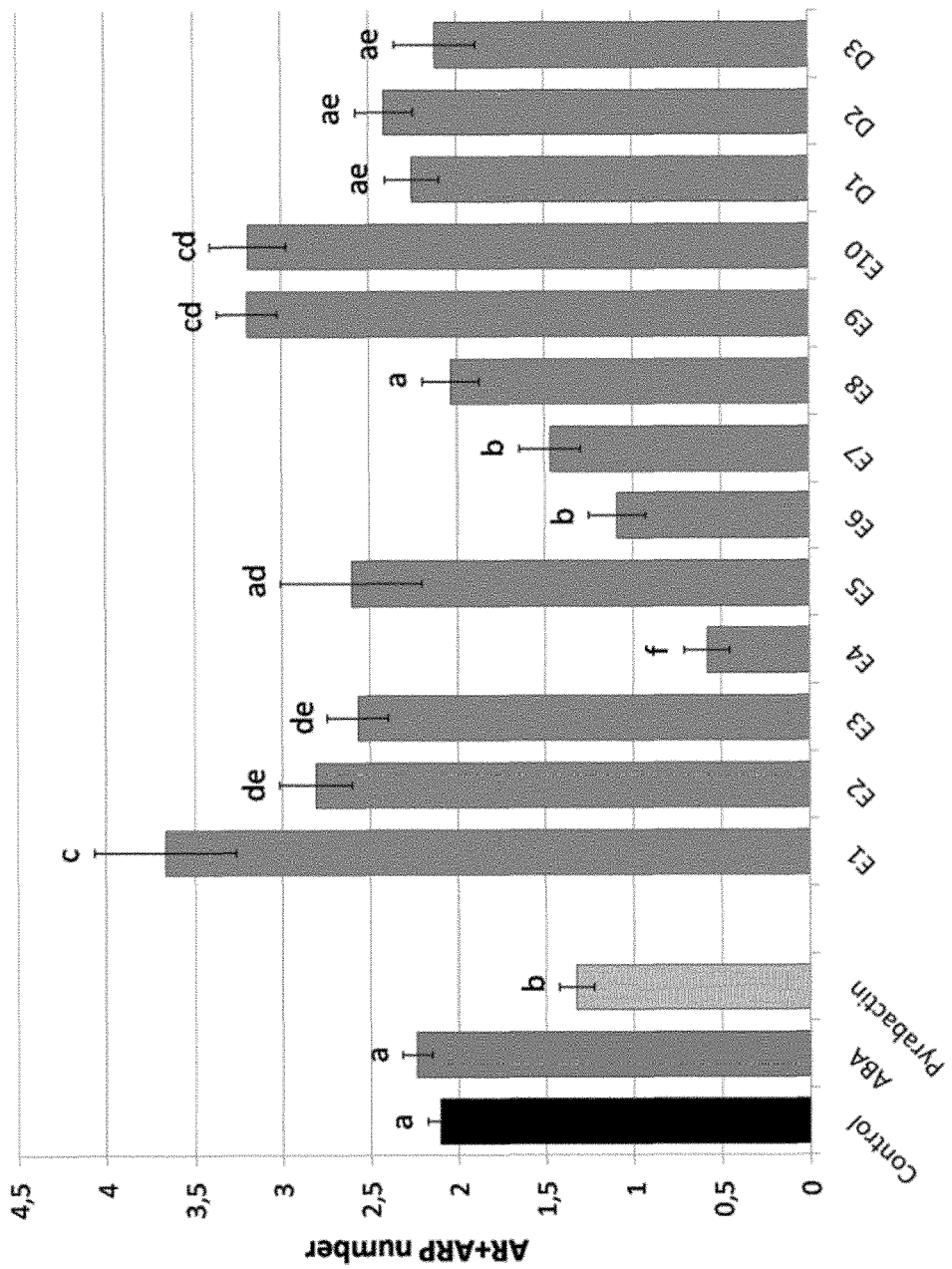
FIG. 3: Adventitious root initiation in etiolated *Arabidopsis thaliana* seedlings growing on ABA-, pyrabactin- or pyrabactin analogue-medium. The compounds were supplied at 10 μM.

Adventitious root organogenesis was not affected by ABA, but pyrabactin reduced the formation of these roots (FIG. 3). The different analogues evaluated showed a wide range of effects including stimulation and inhibition of adventitious root formation. Three analogues, E4, E6 and E7 gave a reduction of adventitious root formation, respectively stronger or similar to pyrabactin. These three molecules were additionally tested in a wider concentration range to fully describe their effect on AR formation. The weaker analogues E8 and E2 added at 10 µM respectively had no effect or stimulated AR formation (FIG. 3). Analogue E4 had a strong inhibitory effect on plant development suggesting that it exhibits cellular toxicity at the concentration used.

The Effect of Phosphonamide Analogues on Seed Germination

The *Arabidopsis thaliana* Seed Germination Assay

The germination assay in *Arabidopsis thaliana* seeds exists of mature seeds incubated on hormone-containing medium during the stratification (4 d at 5° C.) and the following growth in the growth room. Seed germination is evaluated after 10 d in the growth room (25° C., 70 µmol/m$^2$s, 16 h light/8 h dark). Germination was scored as a percentage representing ratio of the number of germinated seeds to the total seeds initially spread on the plate. ABA and pyrabactin were screened at different concentrations. Both inhibited seed germination and the inhibition was gradual and dose-dependent. At 50 µM, ABA inhibited seed germination stronger than pyrabactin. This is in agreement with previously published results (Puli & Raghavendra, 2012).

Figure 4:
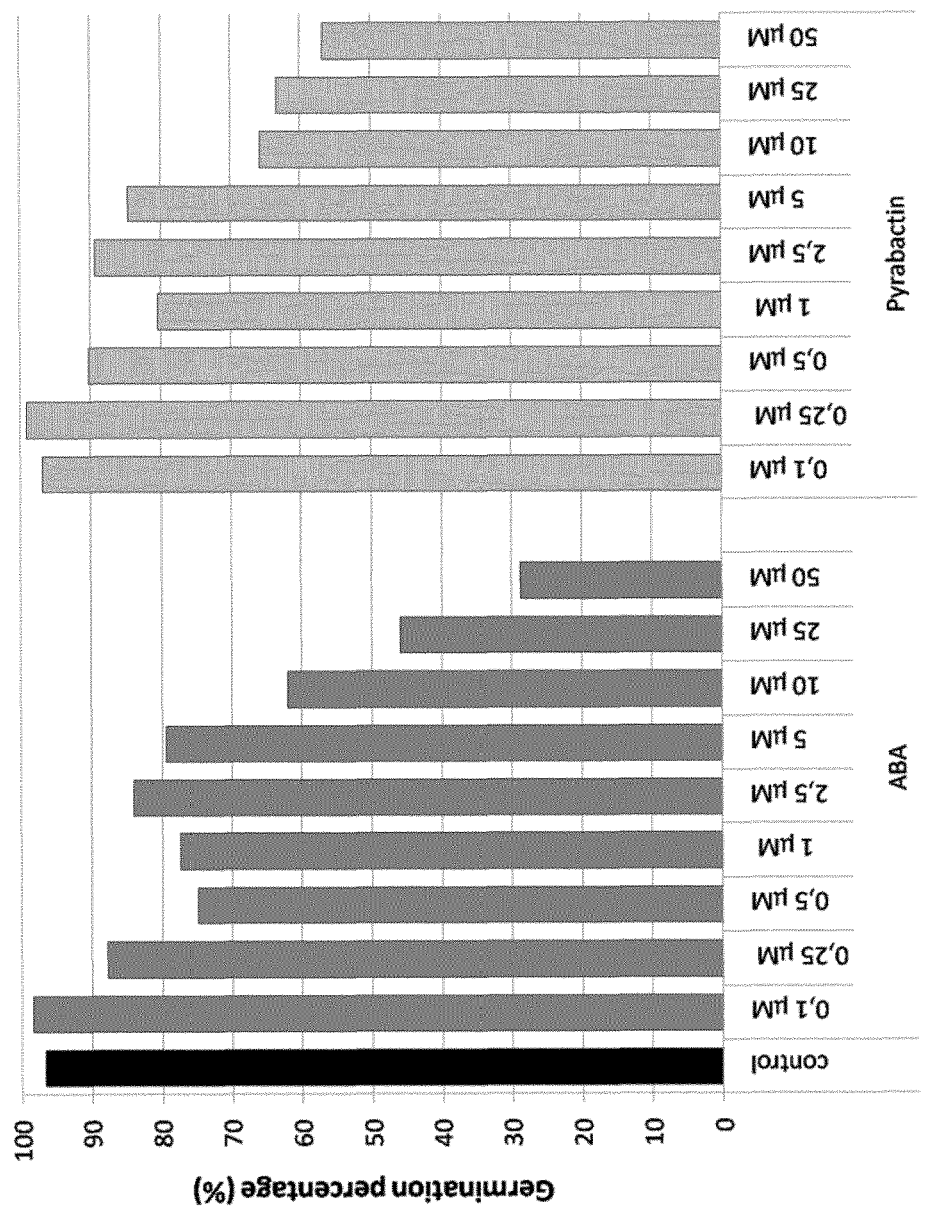
FIG. 4: Germination percentages at different concentrations of respectively ABA and pyrabactin.

However, the response to both molecules is very similar which confirms the ABA-like action of pyrabactin during seed germination (FIG. 4).

Figure 5:
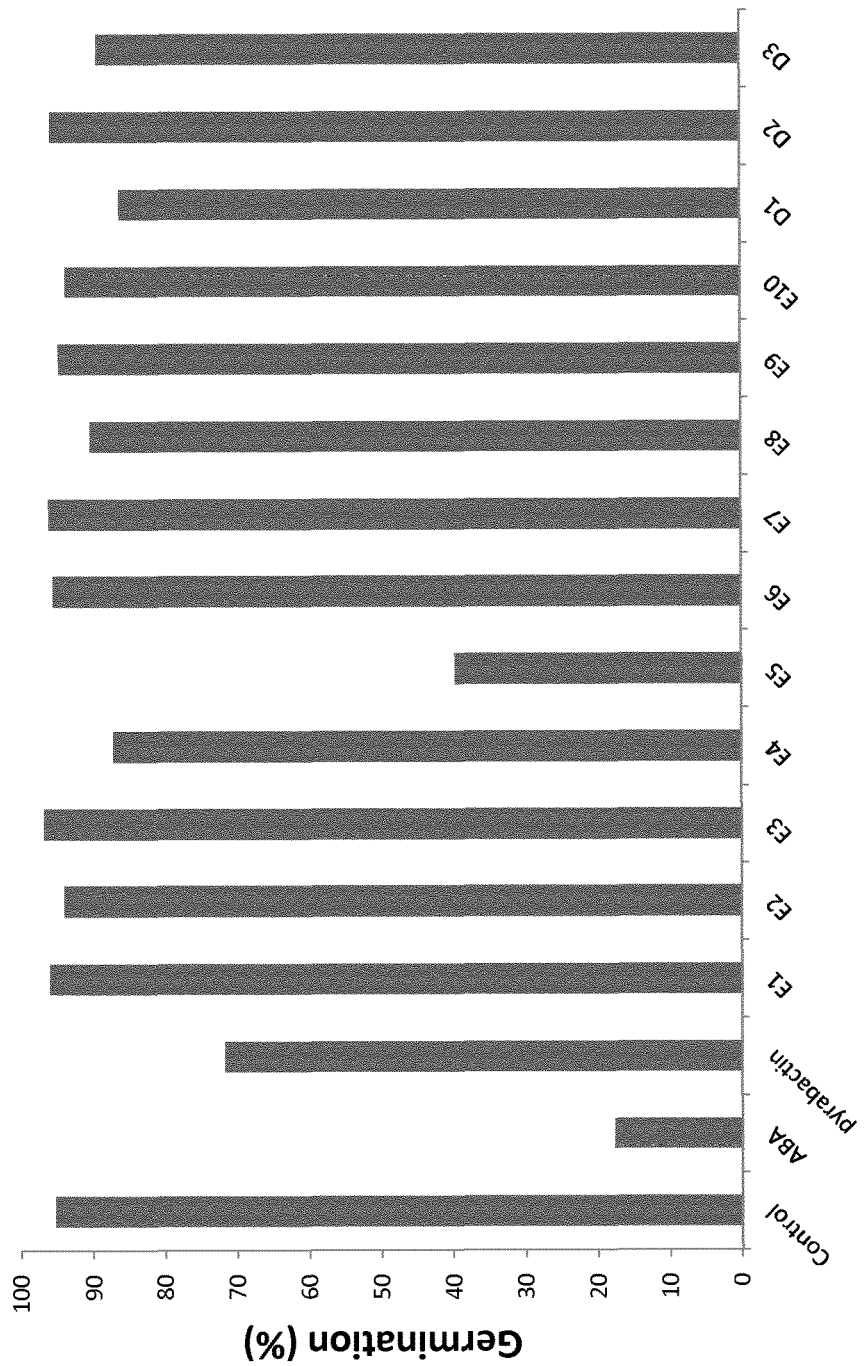
FIG. 5: Germination percentages obtained at 10 μM concentration of the different pyrabactin analogues.

We analysed the effect of phosphonamide pyrabactin analogues of the present invention at 10 μM and compared it with that of ABA and pyrabactin. The phosphonamide pyrabactin analogues were poor inhibitors of germination as only 1 compound, E5 showed significant reduction of the percentage of germinating seeds (FIG. 5).

The Effect of Phosphonamide Analogues on Seedling Development

*Arabidopsis thaliana* Seedling Development

Figure 6:
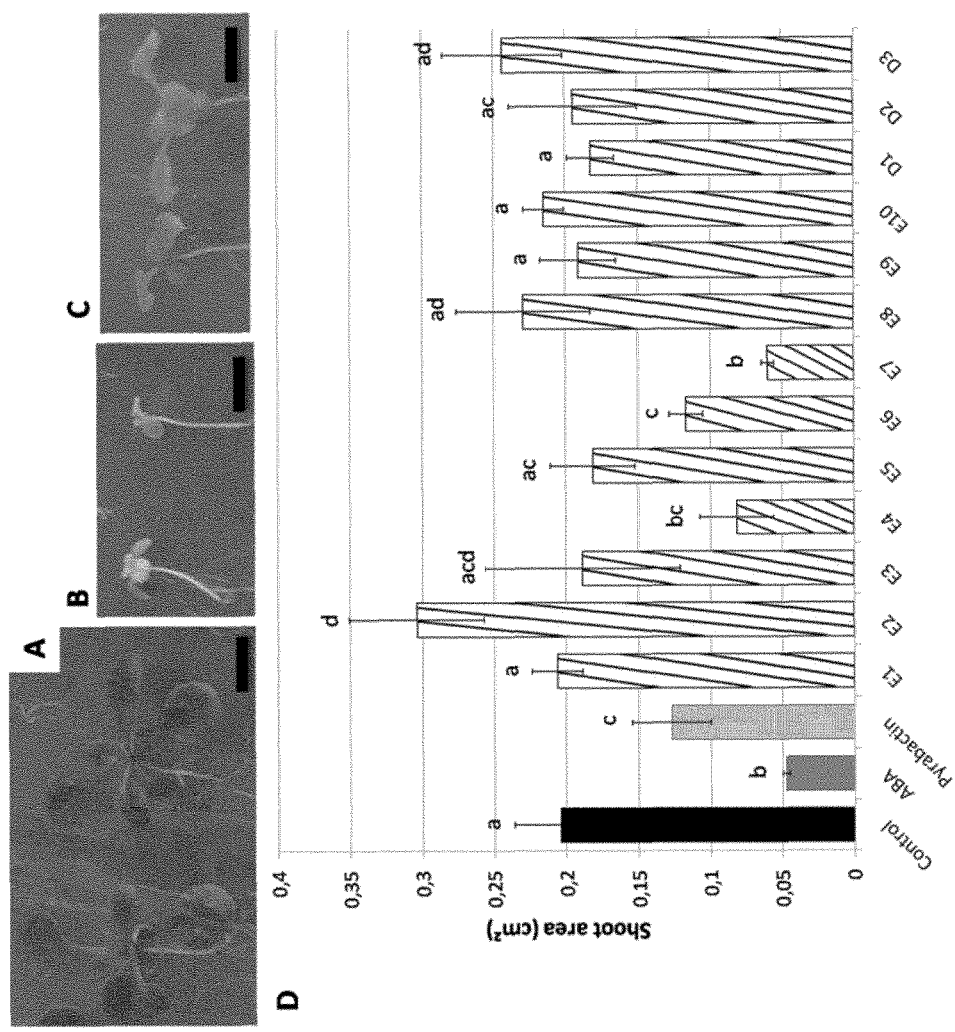
FIG. 6: A. Shoot phenotype of control seedlings grown on basal, hormone-free medium. B. Seedlings growing on 10 μM ABA-medium show a reduced number of newly initiated leaves, the leaf area is smaller and the chlorophyll content of the leaves is affected. C. 10 μM pyrabactin also affects the shoot growth and results in seedlings with a smaller shoot than control seedlings. D. The average shoot area per seedlings is measured using ImageJ. Bars in the graph with a different letter code are significantly different numbers.

We also analysed shoot development in the presence of ABA, pyrabactin and the phosphonamide analogues of the present invention. In the presence of ABA, both the initiation of new leaves and their size was reduced in comparison with control, non-treated seedlings (FIG. 6 A, B). Pyrabactin on the other hand did not affect shoot development as strongly as ABA, but the leaf size was also significantly reduced when pyrabactin was applied at 10 μM concentration (FIG. 6 C).

The effect of the different pyrabactin analogues on shoot growth was also recorded. Especially the compounds E4 and E7 resulted in strong inhibition of the seedling's shoot development. In E4 treated seedlings, the leaves turned yellow and even formed albinos, suggesting a reduction in chlorophyll. In addition, there was an overall reduction in development. E6 resulted in an inhibition of leaf size comparable with pyrabactin. Compound E2 stimulated the development of leaves in comparison with the control. The compounds E4 and E6 did not inhibit the germination but they might be phytotoxic for *Arabidopsis* seedlings because when applied at high doses, the leaves turned white and further development was delayed. The other compounds had no significant effect on seedling shoot development (FIG. 6 D).

The Effect of Phosphonamide Analogues on Stomatal Closure

Leaf Dehydration Assay

ABA-pretreatment results in stomatal closure and therefore protects leaves from excess evaporation of water via the stomatal pores during drought. This anti-transpirant characteristic of ABA is important because drought and water-limitations are the most important factors limiting crop-productivity, resulting up to 50% yield losses worldwide (Jones & Corlett, 1992; Skirycz & Inzé, 2010). In untreated leaves, the water potential declines rapidly when the leaves are exposed to drought. Preconditioning these leaves with ABA prevents water deficits by closing the stomata and membrane-leakage (Clifford et al, 1998; Islam et al, 2003). Water loss can be followed by measuring leaf weight. Samples pre-treated with ABA showed significantly less weight loss due to the reduction of water evaporation. The relative water content can be determined by the fresh weight, turgid weight (=mass after rehydration) and dry weight (Clifford et al, 1998). The dehydration assay was designed following this principle. *Nicotiana benthamiana* leaves were removed from 8 w old ex vitro plants. The detached leaves were kept turgid by dipping the petioles in water during 1 h. This way optimal feeding into the xylem occurred. Next, the leaves were removed from the solutions and the petiole-ends were sealed with silicon and covered with parafilm to prevent water loss via the venation system. The fully turgid leaves were subsequently exposed to an air flow in a laminar flow cabinet. Water loss was monitored during 6 h by periodic measurement of the wet leave weight.

Figure 7:
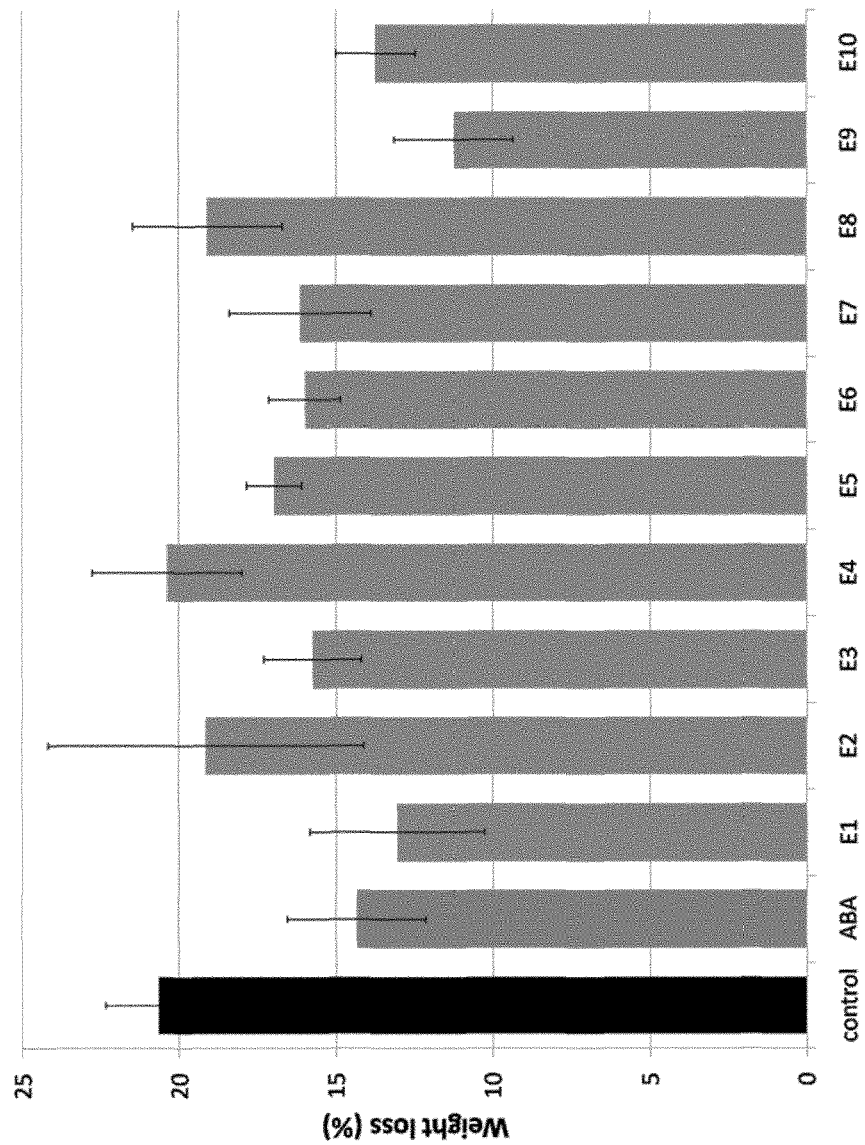
FIG. 7: Average weight loss of leaves pre-treated with 10 μM ABA or the pyrabactin analogues E1-E10 after 6 hours of exposure to a dry air flow.

Using this assay, we analysed the protection against water loss by ABA pre-treatments with 10 and 100 μM. ABA treatment resulted in significantly less weight loss, demonstrating its capacity to reduce water loss (Table 1). Pre-treatments with pyrabactin analogues was at 10 μM concentration and five to ten replicate leaves were incubated in aquatic solutions containing the respective compounds. Their average weight loss is represented in FIG. 7. Similarly to ABA, compounds E1, E9 and E10 resulted in a reduction of transpiration. The other compounds evaluated were not significantly different to the control leaves (FIG. 7).

TABLE 1

% weight loss of ABA-pretreated leaves. The values given indicated averages of 5-10 leaves and the standard error indicates the significance between the different treatments.

| Treatment | % weight loss (average) | Standard error |
|---|---|---|
| Control | 29.51% | 2.28 |
| 10 μM ABA | 18.54% | 3.94 |
| 100 μM ABA | 16.99% | 1.87 |

Stomatal Closure Assay

Further support for ABA-like action of pyrabactin analogues followed from stomatal aperture measurements. In stomata, the accumulation of ABA results in the closure of leaf pores. The plants can then more efficiently manage available water resources. As a measure for drought response and ABA-like activity, stomatal closure was studied in tobacco (*Nicotiana tabacum*) and *Arabidopsis thaliana* (Jones & Mansfiel. T, 1970; Roelfsema & Prins, 1995; Thomas, 1970). For this assay we used tobacco epidermal strips (taken at the abaxial side of the leaves) fixed on a microscopic slide under a cover slip. The epidermal strips were brought into contact with a buffer (10 mM MES, 50 mM KCl, 10 μM $CaCl_2$ and pH 6.5) and the slides were put in the light during 2 h to ensure optimal opening of the stomata. The stomatal opening was measured using a microscope with automated table (Olympus, CellM™-Software). Stomates were imaged at fixed positions every 5 min during 1 hour. At the start of the experiment the epidermal strips were treated with a solution containing compounds and a drop of bromo-phenol blue to monitor the perfusion process (solution exchange was triggered by absorbing solution at one end with filter paper).

Figure 8:
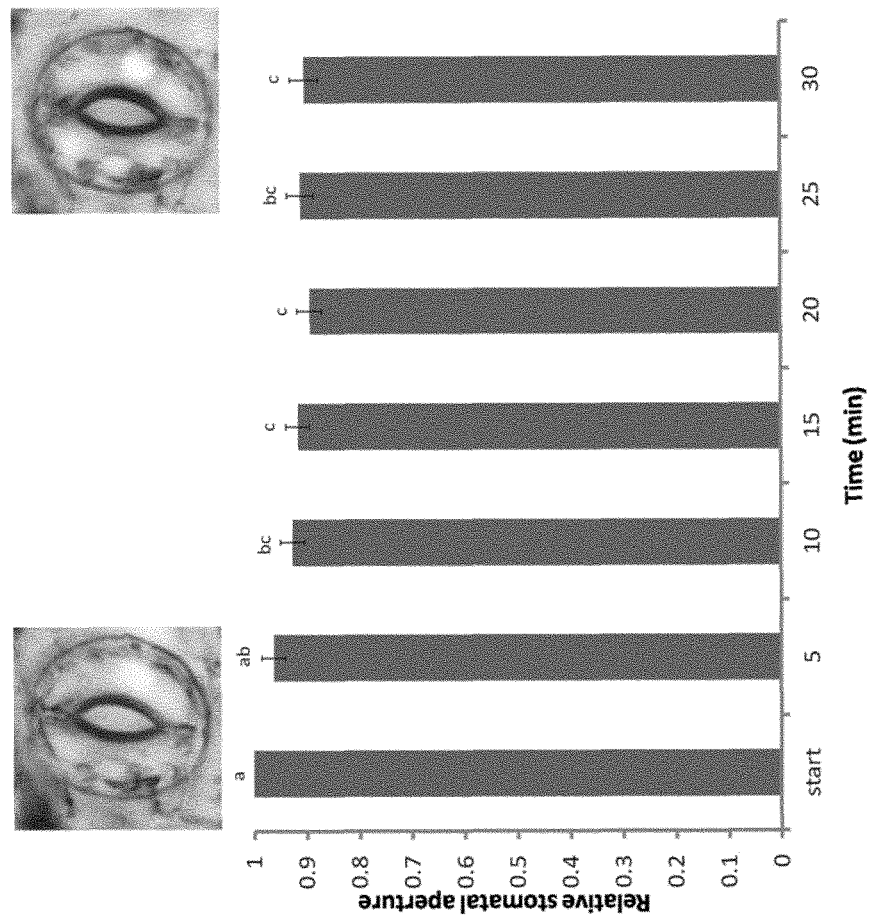
FIG. 8: Relative stomatal aperture of control stomata followed during 30 minutes in the absence of compounds. The values indicated are relative to the stomatal aperture measured at the start of the experiment.

In the absence of compounds a reduction of stomatal aperture of approximately 10% was observed of after 15 minutes with no further change up to 30 minutes (FIG. 8). Therefore 10% stomatal closure was considered as not significant.

Figure 9:
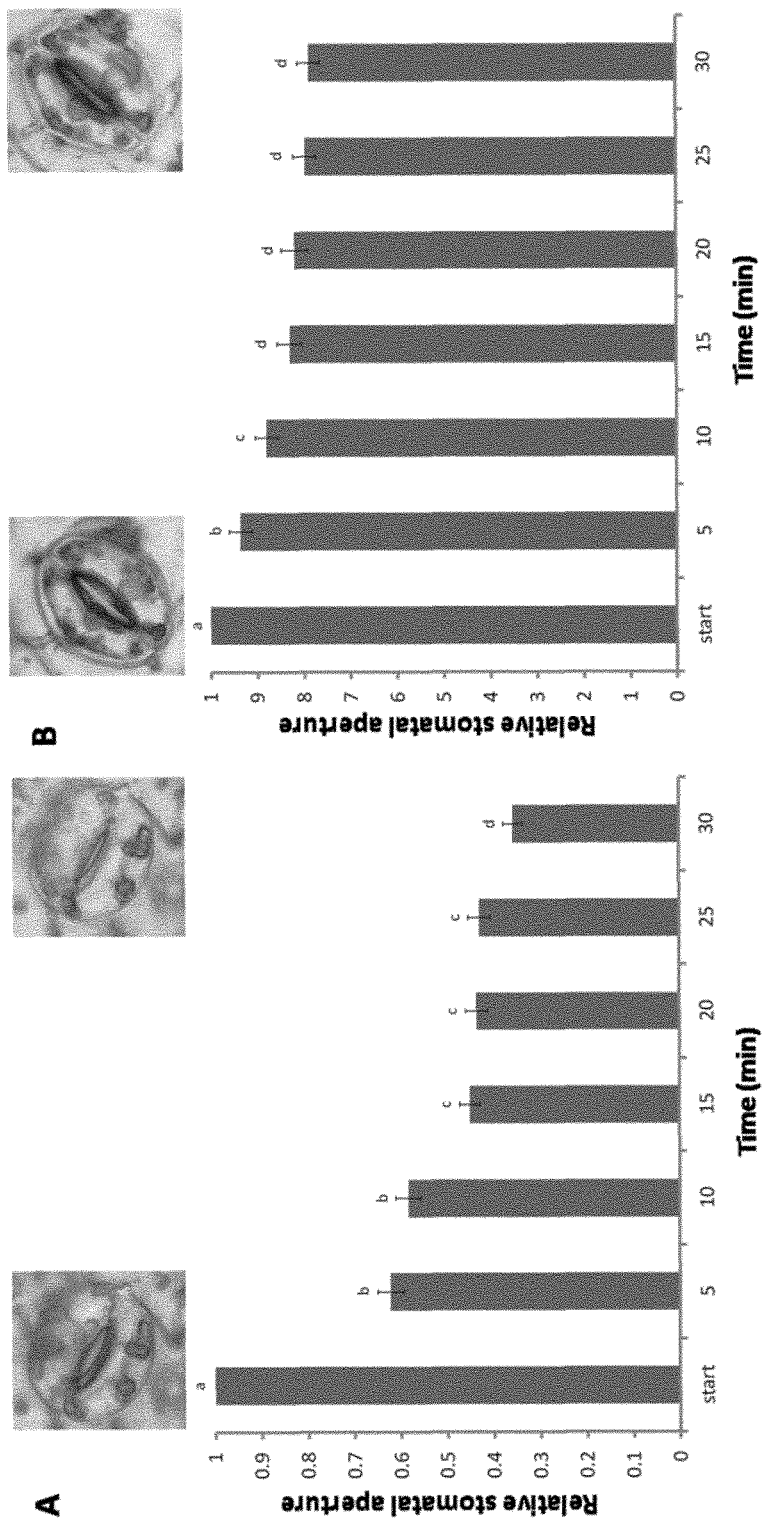
FIG. 9: A. 10 μM ABA, rapidly induces stomatal closure. B. Epidermal leaf strips treated with 10 μM pyrabactin in solution demonstrated an effect on the stomata.

ABA was highly effective in reducing the stomatal opening within 5 min reaching a relative aperture of 40% (FIG. 9 B). Similarly to in pea (Puli & Raghavendra, 2012), pyrabactin induced stomatal closure, rapidly but to a much lower degree than ABA (FIG. 9 B).

Figure 10:
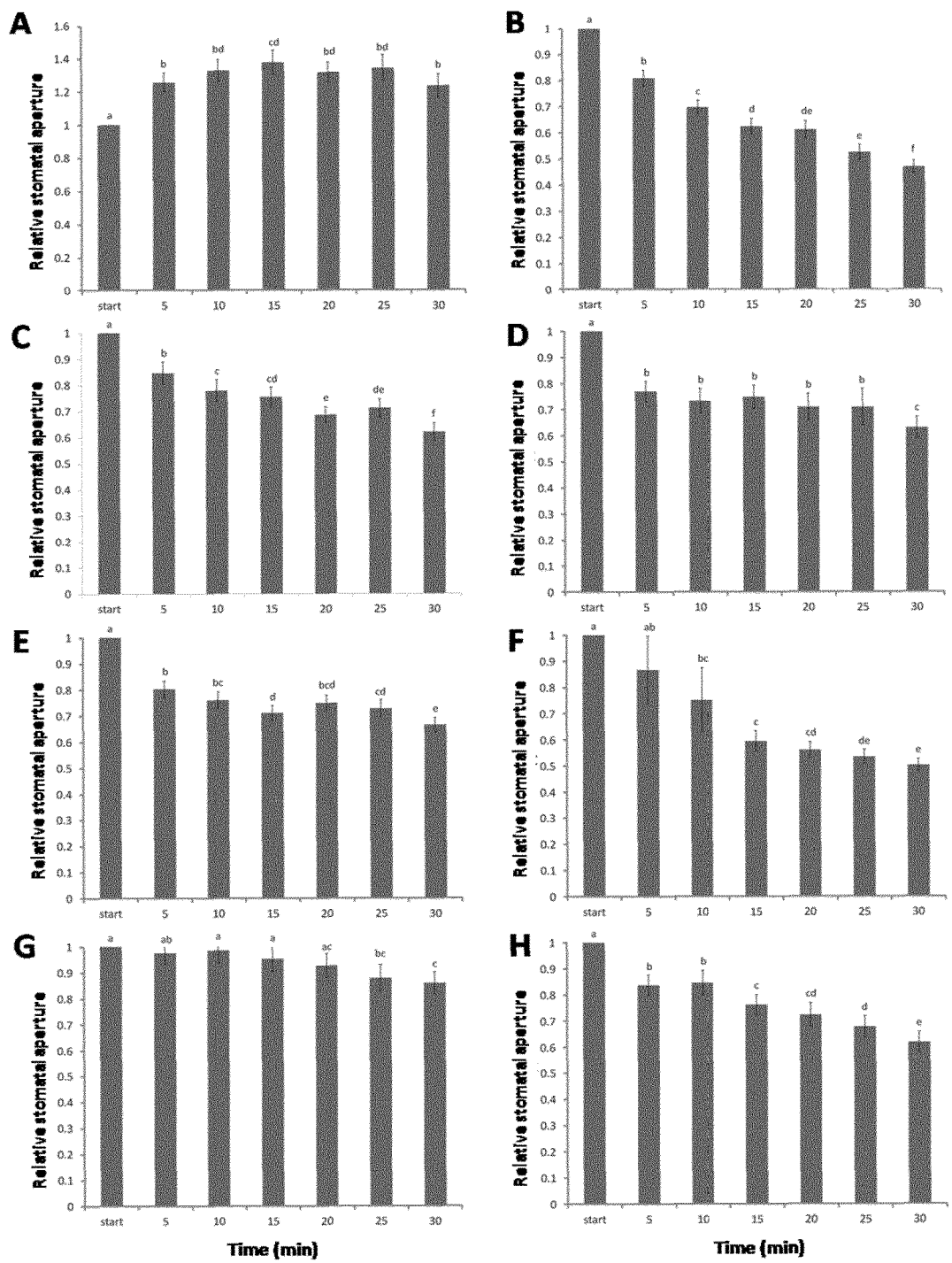
FIG. 10: Relative stomatal aperture following treatment of A. E1, B. E2, C. E3, D. E4, E. E5, F. E6, G. E7, H. E8, I. E9, J. E10, K. D1, L. D2 and M. D3. All compounds are evaluated at 10 μM concentration.

In subsequent experiments, the action of pyrabactin analogues of the present invention was assessed. We found active and inactive compounds (FIG. 10). Compound E1 did not cause closure of the stomata and even induced the opening when we include the intrinsic closure of 10% in untreated stomata (see above, FIG. 10 A). E2 on the other hand induced stomata closure to 50% of the start opening, but the speed at which the stomata close is lower than for ABA: In the presence of 10 μM ABA the stomata closed within 10 minutes (50% of closure) while for E2, this was only obtained after 30 minutes (FIG. 10 B). Also analogue E6 strongly induced stomatal closure (FIG. 10 F). Other compounds also caused intermediate stomatal closure: E3, E4, E5, E8, E10 and D3 (FIG. 10 C, D, E and H). E7, E9, D1 and D2 in contrary did not affect the size of the stomatal aperture (FIG. 10 G).

Unlike ABA and ABA-agonists, compound E1 induced stomatal opening, suggesting that this molecule does not induce the typical ABA signalling process in the stomata. This effect is intriguing, as this was not observed with other ABA agonists reported. We suggest that the mode of action of E1 is different from that of other pyrabactin analogous and that it may influence ABA signalling by inactivating ABA perception or generate opposite downstream regulation by an alternative interaction with the PYR/PYL receptors. In general the pyrabactin analogues do exert ABA-like responses, confirming that they likely act as ABA-agonists. The results further show that stomatal aperture may be regulated by means of exposure to synthetic molecules either to enhance water evaporation or to reduce it. Hence these molecules are very useful in molecular studies to determine the signalling complexes and pathways involved in stomatal regulation. Moreover, as the compounds show a certain level of specificity they are helpful in improving agricultural applications.

Agricultural Application of the Pyrabactin Analogues of the Present Invention

To maintain their performance in suboptimal conditions, plants, as sessile organisms, depend on endogenous signals to switch on protective pathways (Raghavendra et al, 2010). Manipulations of these pathways is therefore astrategy to assure plant production and ABA is the target molecule to use. Topical spraying of ABA results in the closure of stomata and the protection against drought stress, but it also affects primary root growth and leaf development. The pyrabactin analogues of present invention solve these limitations.

TABLE 2

Overview of the biological responses of the different pyrabactin analogues. All the molecules are applied at 10 μM concentration and compared with control not-treated seeds, seedlings or epidermal strips.

| Analogue | Seed germination | PR | LR | AR | Shoot | Stomata |
|---|---|---|---|---|---|---|
| ABA | +++ | +++ | +++ | 0 | +++ | +++ |
| Pyrabactin | ++ | ++ | ++ | +++ | ++ | + |
| E1 | 0 | + | ++ | − | 0 | − |
| E2 | 0 | 0 | + | − | − | +++ |
| E3 | 0 | 0 | + | − | 0 | ++ |
| E4 | + | +++ | +++ | +++ | +++ | ++ |
| E5 | +++ | + | + | 0 | 0 | + |
| E6 | 0 | ++ | +++ | +++ | ++ | +++ |
| E7 | 0 | +++ | +++ | +++ | +++ | 0 |
| E8 | 0 | 0 | +− | 0 | 0 | ++ |
| E9 | 0 | 0 | + | − | 0 | 0 |
| E10 | 0 | + | + | − | 0 | + |
| D1 | + | 0 | +− | 0 | 0 | + |
| D2 | 0 | 0 | 0 | 0 | 0 | 0 |
| D3 | 0 | 0 | 0 | 0 | 0 | 0 |

The individual data are represented above. 0 = not significantly different to control, +++ = very strong action (inhibition for seeds, roots and shoots or induction of stomatal closure), ++ = strong action, + = intermediate action and − = opposite action (e.g. stimulans of seeds, roots and shoots or opening of the stomata).

In climates with a humid late-summer, pre-harvest sprouting of the seeds causes significant losses (Gubler et al, 2005). Spraying ABA, as an inhibitor of seed germination on the crops vulnerable for this problem could solve the sprouting issues. However, ABA also induces other effects in the plants. Since this is not-desired, the application of more specific molecules is a solution to the latter problem. Among the analogues screened, one molecule E5 specifically inhibits seed germination, but has limited effect on the other biological responses screened (Table 2). Another interesting analogue is E2, which affects stomatal closure and has positive effects on shoot development and adventitious root formation. Also E8 is a good compound to spray on crops to enhance the plant's tolerance to drought without affecting root growth. In contrary to ABA, this is positive for the development of a plant in prolonged stress conditions because the root growth would be maintained which assures the access to deeper water sources. It is therefore concluded that these compounds offer new possibilities for field applications in agriculture.

REFERENCES

Antoni R, Rodriguez L, Gonzalez-Guzman M, Pizzio G A, Rodriguez PL (2011) News on ABA transport, protein degradation, and ABFs/WRKYs in ABA signaling. *Curr Opin Plant Biol* 14: 547-553

Ashokan K V (2010) Docking studies on abscisic acid receptor pyrabactin receptor 1 (pyr1) and pyrabactin like receptor (pyl1). *International Journal of Environmental Sciences* 1: 314-322

Audus L. J. and Quasterl J. H. (1948). The Growth-inhibitory Activity of the Sulphonamides and Plant Growth-substances, and the Effects thereon of p-Aminobenzoic acid. *Ann Bot* 12: 27-34

Clifford S C, Arndt S K, Corlett J E, Joshi S, Sankhla N, Popp M, Jones H G (1998) The role of solute accumulation, osmotic adjustment and changes in cell wall elasticity in drought tolerance in *Ziziphus mauritiana* (Lamk.). *J Exp Bot* 49: 967-977

Crowdy S. H. and Jones D. R. (1956). Partition of Sulphonamides in Plant Roots: A Factor in their Translocation. *Nature* 178, 1165-1167

Cutler S R, Park S Y, Defries A. (2010) Control of plant stress tolerance, water use efficiency and gene expression using novel ABA receptor proteins and synthetic agonists Regents of the University of California, USA.

Daszkowska-Golec A, Szarejko I. (2013). Open or close the gate—stomata action under the control of phytohormones in drought stress conditions. Front Plant Sci. 4:138

Finkelstein R R, Gampala S S L, Rock C D (2002) Abscisic acid signaling in seeds and seedlings. *Plant Cell* 14: S15-S45

Garciarrubio A, Legaria J P, Covarrubias A A (1997) Abscisic acid inhibits germination of mature *Arabidopsis* seeds by limiting the availability of energy and nutrients. *Planta* 203: 182-187

Gubler F, Millar A A, Jacobsen J V (2005) Dormancy release, ABA and pre-harvest sprouting. *Curr Opin Plant Biol* 8: 183-187

Hao Q, Yin P, Yan C, Yuan X, Li W, Zhang Z, Liu L, Wang J, Yan N. (2010). Functional mechanism of the abscisic acid agonist pyrabactin. *J Biol Chem.* 285:28946-52.

Hubbard K E, Nishimura N, Hitomi K, Getzoff E D, Schroeder J I (2010) Early abscisic acid signal transduction mechanisms: newly discovered components and newly emerging questions. *Genes Dev* 24: 1695-1708

Islam M A, Blake T J, Kocacinar F, Lada R (2003) Ambiol, spermine, and aminoethoxyvinylglycine prevent water stress and protect membranes in *Pinus strobus* L under drought. *Journa of Experimental Botany* 17: 278-284

Jones H G, Corlett J E (1992) Current topics in drought physiology. *Journal of Agricultural Science* 119: 291-296

Jones R J, Mansfiel. T (1970) Suppression of stomatal opening in leaves treated with abscisic acid. *J Exp Bot* 21: 714-&

Joshi-Saha A, Valon C, Leung J. (2011) Abscisic acid signal off the STARting block. Mol Plant. 2011 July; 4(4):562-80

Kitahata N, Asami T. (2011) Chemical biology of abscisic acid. *J Plant Res.* 124:549-57

Linkies A, Leubner-Metzger G (2012) Beyond gibberellins and abscisic acid: how ethylene and jasmonates control seed germination. *Plant Cell Reports* 31: 253-270

Melcher K, Ng L M, Zhou X E, Soon F F, Xu Y, Suino-Powell K M, Park S Y, Weiner J J, Fujii H, Chinnusamy V, Kovach A, Li J, Wang Y H, Li J Y, Peterson F C, Jensen D R, Yong E L, Volkman B F, Cutler S R, Zhu J K, Xu H E (2009) A gate-latch-lock mechanism for hormone signalling by abscisic acid receptors. *Nature* 462: 602-U672

Melcher K, Zhou X E, Xu H E. (2010a) Thirsty plants and beyond: structural mechanisms of abscisic acid perception and signaling. *Curr Opin Struct Biol.* 20:722-9.

Melcher K, Xu Y, Ng L M, Zhou X E, Soon F F, Chinnusamy V, Suino-Powell K M, Kovach A, Tham F S, Cutler S R, Li J, Yong E L, Zhu J K, Xu H E. (2010). Identification and mechanism of ABA receptor antagonism. *Nat Struct Mol Biol.* 17:1102-8.

Mosquna A, Peterson F C, Park S Y, Lozano-Juste J, Volkman B F, Cutler S R. (2011). Potent and selective activation of abscisic acid receptors in vivo by mutational stabilization of their agonist-bound conformation. *Proc Natl Acad Sci USA.* 108:20838-43.

Nambara E, Okamoto M, Tatematsu K, Yano R, Seo M, Kamiya Y (2010) Abscisic acid and the control of seed dormancy and germination. *Seed Sci Res* 20: 55-67

Park S Y, Fung P, Nishimura N, Jensen D R, Fujii H, Zhao Y, Lumba S, Santiago J, Rodrigues A, Chow T F, Alfred S E, Bonetta D, Finkelstein R, Provart N J, Desveaux D, Rodriguez P L, McCourt P, Zhu J K, Schroeder J I, Volkman B F, Cutler S R (2009) Abscisic acid inhibits type 2C protein phosphatases via the PYR/PYL family of START proteins. *Science* 22: 1068-1071

Peterson F C, Burgie E S, Park S Y, Jensen D R, Weiner J J, Bingman C A, Chang C A, Cutler S R, Phillips G N J, Volkman B F (2010) Structural basis for selective activation of ABA receptors. *Nat Struct Mol Biol* 17: 1109-1113

Puli M R, Raghavendra A S (2012) Pyrabactin, an ABA agonist, induced stomatal closure and changes in signalling components of guard cells in abaxial epidermis of *Pisum sativum. J Exp Bot* 63: 1349-1356

Roelfsema M R G, Prins H B A (1995) Effect of abscisic acid on stomatal opening in isolated epidermal strips of abi mutants of *Arabidopsis thaliana. Physiol Plant* 95: 373-378

Sreenivasulu, N., Harshavardhan, V. T., Govind, G., Seiler, C., Kohli, A. (2012), 'Contrapuntal role of ABA: Does it mediate stress tolerance or plant growth retardation under long-term drought stress?'. *Gene,* 506:265-273.

Skirycz A, Inzé D (2010) More or less: plant growth under limited water. *Current Opinion in Biotechnology* 21: 197-203

Thomas D A (1970) The regulation of stomatal aperture in Tobacco leaf epidermal strips. *Australian Journal of Biological Sciences* 23: 961-980

Tilman D, Balzer C, Hill J, Befort B L. (2011) Global food demand and the sustainable intensification of agriculture. *Proc Natl Acad Sci USA.* 108:20260-4.

Mucha A, Kunert A, Grembecka J, Pawelczak M, Kafarski P (2006) A phosphonamidate containing aromatic N-terminal amino group as inhibitor of leucine aminopeptidase—design, synthesis and stability. European Journal of Medicinal Chemistry 41: 768-772.

Xie L, Ding Y, Wang Y, Ding Y (2009) Synthetic strategy of o-hydroxyphenyl(ethynyl)phosphinates. Chinese Journal of Chemistry 27: 1387-1390.

Zhang, W. and Gusta, L. V. (2010). Germination response of black and yellow seed coated canola (*Brassica napus*) lines to chemical treatments under cold temperature conditions. Plant Growth Regulation 60:105-114.

The invention claimed is:

1. A compound—or its salt—of the formula:

wherein:

n is 1;

X is H, Br, or F;

Y is NH or O;

Z is Et or H;

A, B, and C are CH or N; and at least one of A, B, or C is N.

2. An agricultural chemical formulation formulated for contacting to plants, the formulation comprising a compound according to claim 1.

3. A formulation according to claim 2 further comprising at least one of a herbicide, fungicide, pesticide, fertilizer or surfactant.

4. A method of modulating plant development, the method comprising contacting a plant with a sufficient amount of the formulation according to claim 2 to modulate the development of said plant compared to not contacting the plant with said formulation.

5. A method according to claim 4 wherein said modulating is increasing the tolerance to drought stress.

6. A compound of the formula as given for E2, E3, E5 or E8:

E2
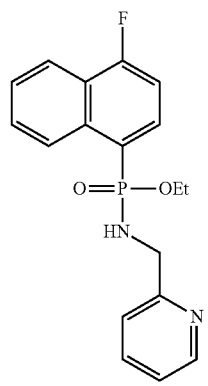

E3
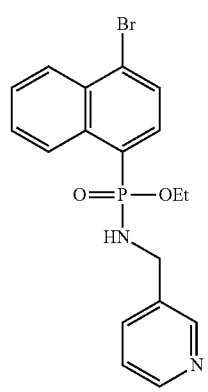

E5
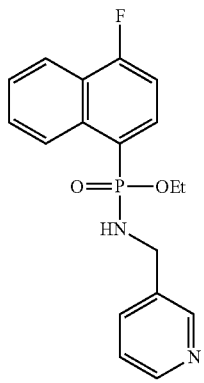

E8
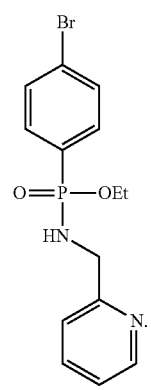

7. A method of specifically inducing stomatal closure in a plant without affecting root or shoot growth, the method comprising contacting the plant with a sufficient amount of at least one of the compound E2, E3 or E8 of claim 6.

8. A method of specifically inhibiting seed germination in a plant, the method comprising contacting the plant with a sufficient amount of the compound E5 of claim 6.

* * * * *